United States Patent [19]

Hirakawa et al.

[11] Patent Number: 4,977,267

[45] Date of Patent: Dec. 11, 1990

[54] INTERMEDIATES FOR PYRIDYLOXY COMPOUNDS HAVING UTILITY AS ANTI-PEPTIC ULCER AGENTS

[75] Inventors: Nobuhiko Hirakawa, Kokubunji; Noriaki Kashiwaba, Kawasaki; Hajime Matsumoto, Hino; Akihiko Hosoda, Shiki; Yasuo Sekine, Yokohama; Yoshikazu Isowa, Tokyo; Tetsuaki Yamura, Niiza; Akihiro Sekine, Kyoto; Masashi Nishikawa, Higashikurume, all of Japan

[73] Assignee: Fujirebio Kabushiki Kaisha, Tokyo, Japan

[21] Appl. No.: 301,856

[22] Filed: Jan. 26, 1989

Related U.S. Application Data

[62] Division of Ser. No. 166,022, Mar. 9, 1988, Pat. No. 4,912,101.

[30] Foreign Application Priority Data

Mar. 13, 1987 [JP] Japan ................................. 62-56434
Nov. 17, 1987 [JP] Japan ................................. 62-288331
Nov. 17, 1987 [JP] Japan ................................. 62-288332

[51] Int. Cl.$^5$ ................. C07D 401/12; C07D 403/14; C07D 405/12; C07F 7/02
[52] U.S. Cl. .................................. 546/272; 546/14; 546/268; 546/283; 546/284
[58] Field of Search ................ 546/283, 272, 268, 14, 546/284

[56] References Cited

FOREIGN PATENT DOCUMENTS 0003677 8/1979 European Pat. Off. ............ 544/319
0069664 1/1983 European Pat. Off. ............ 514/471
0172968 3/1986 European Pat. Off. ............ 544/60
0177016 4/1986 European Pat. Off. ............ 544/316

Primary Examiner—Alan L. Rotman
Attorney, Agent, or Firm—Sherman and Shalloway

[57] ABSTRACT

The compounds of the formulas (VI) and (VII) are useful intermediates in producing pyridyloxy derivatives of the formula (I), such as, for instance, N-{4-[4-(piperidinomethyl)pyridyl-2-oxy]-2-butenyl}-2-(furfurylthio)acetamide, which are useful as anti-peptic ulcer agents. The compounds of formula (VI) have the formula

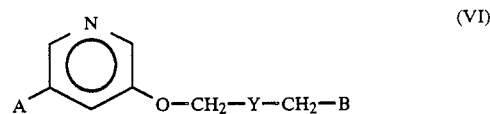

(VI)

wherein A represents a formyl group, a protected formyl group, a hydroxymethyl group or a protected hydroxymethyl group. The compounds of formula (VIII) have the formula

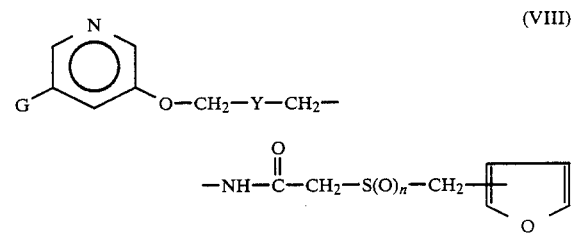

(VIII)

wherein G represents a formyl group, a protected formyl group, a hydroxymethyl group, a hydroxymethyl group in which the hydroxyl group is protected, or a halogenomethyl group, Y represents —CH$_2$—CH$_2$— or —CH=CH—, and n is 0, 1 or 2.

20 Claims, No Drawings

INTERMEDIATES FOR PYRIDYLOXY COMPOUNDS HAVING UTILITY AS ANTI-PEPTIC ULCER AGENTS

This is a divisional application of prior application Ser. No, 166,022, filed Mar. 9, 1988, now issued as U.S. Pat. No. 4,912,101.

This invention relates to novel pyridyloxy derivatives, and more specifically to compounds of the following formula (I), or salts thereof,

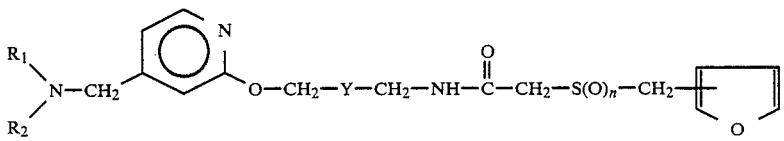
(I)

wherein each of $R_1$ and $R_2$ represents a lower alkyl group, or $R_1$ and $R_2$, together with the nitrogen atom to which they are bonded, may form a substituted or unsubstituted, saturated or partially unsaturated 4- to 8-membered heterocyclic group which may contain a hetero atom selected from N, O and S, Y represents a group of the formula $-CH_2-CH_2-$ or $-CH=CH-$, and n is 0, 1 or 2, processes for production thereof, use thereof as a drug, particularly antiulcer agent, and intermediates useful for production of the compounds of formula (I).

The greatest cause of ulcer formation in the stomach or duodenum is regarded as excessive secretion of gastric acid, and compounds having anti-cholinergic activity or compounds which neutralize gastric acid have been proposed as antiulcer agents. The anticholinergic compounds, however, are no longer used generally as antiulcer agents because of their strong side effects. The drugs for neutralizing gastric acid have a poor duration of effect and have been desired to be improved.

It is known that secretion of gastric acid is caused by stimulation of a histamine $H_2$ receptor, and the administration of a drug having histamine $H_2$ receptor antagonizing activity inhibits secretion of gastric acid and is useful for therapy and treatment of peptic ulcer. Certain substituted pyridyloxy derivatives have been suggested as drugs having histamine $H_2$ receptor antagonizing activity (European Laid-Open Patent Publication Nos. 87274, 89153, 105702, 172968 and 177016).

For example, European Laid-Open Patent Publication No. 177016 discloses that a compound of the following formula

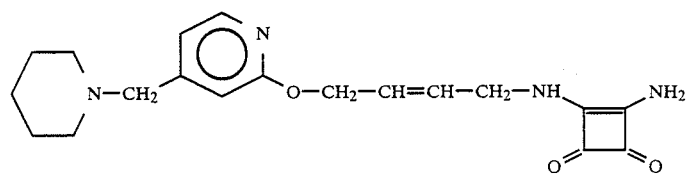

is useful as an antipeptic ulcer agent based on its histamine $H_2$ receptor antagonizing activity. Although this compound has fairly good antiulcer activity, the duration of its histamine $H_2$ receptor antagonizing activity is short and its toxicity is high.

It has been strongly desired to develop a drug having stronger histamine $H_2$ receptor antagonizing activity, i.e. long-lasting high gastric acid secretion inhibiting activity and an action of protecting the mucosa of the digestive organs, which are the desirable pharmacological effects of an anti-peptic ulcer agent.

We have extensively made investigations in order to meet this desire, and have now found that compounds of formula (I) given above have gastric acid secretion inhibiting activity based on their excellent histamine $H_2$ receptor antagonizing activity, and an action of protecting the mucosa of the digestive organs, and therefore are useful as an antipeptic ulcer agent.

The term "lower", as used herein to qualify an atomic grouping or a compound, means that the atomic grouping or compound so qualified has not more than 6 carbon atoms, preferably not more than 4 carbon atoms.

Thus, the "lower alkyl group" represented by $R_1$ and $R_2$ in formula (I) may be a liner or branched alkyl group, such as methyl, ethyl, propyl, isopropyl, butyl, isobutyl, sec-butyl, tert-butyl, pentyl, isoamyl and hexyl groups. Examples of the "saturated or partially unsaturated 4- to 8-membered heterocyclic group which may contain a hetero atom selected from N, O and S" include azetidino, pyrrolidino, piperidino, 1-perhydroazepinyl, dihydro-1-pyrrolyl, tetrahydro-1-pyridyl, 1-piperazinyl, morpholino and thiomorpholino. These heterocyclic groups may further contain a substituent on the ring. The substituent may be, for example, a lower alkyl group such as methyl or ethyl, and a hydroxyl group.

A preferred group of compounds of formula (I) provided by this invention are those of formula (I) in which each of $R_1$ and $R_2$ is a lower alkyl group, especially a methyl group, or $R_1$ and $R_2$, taken together with the nitrogen atom to which they are bonded, form a saturated or partially unsaturated 5- to 7-membered heterocyclic group which may be substituted by a lower alkyl group, such as a pyrrolidino, piperidino, 3-methylpiperidino, 1,2,3,6-tetrahydro-1-pyridyl or 1-perhydroazepinyl group, particularly the piperidino group.

Where the group Y is $-CH=CH-$ in formula (I), the compounds may include both cis- and trans-isomers Generally, the cis-isomers are preferred. The bonding site of the furane ring

in formula (I) may be the 2- or 3-position to the methylene group (—CH$_2$—). Usually, when n is 1, the furane ring is preferably bonded to the methylene group at the 2-position. When n is 2, the furane ring is preferably bonded to the methylene group at the 3-position.

Tyical examples of the compounds of formula (I) provided by this invention are given below.

N-{4-[4-(piperidinomethyl)pyridyl-2-oxy]-2-butenyl}-2-(furfurylthio)acetamide,
N-{4-[4-(piperidinomethyl)pyridyl-2-oxy]-2-butenyl}-2-(furfurylsulfinyl)acetamide,
N-{4-[4-(piperidinomethyl)pyridyl-2-oxy]-2-butenyl}-2-(furfurylsulfonyl)acetamide,
N-{4-[4-(piperidinomethyl)pyridyl-2-oxy]-2-butenyl}-2-(3-furylmethylthio)acetamide,
N-{4-[4-(piperidinomethyl)pyridyl-2-oxy]-2-butenyl}-2-(3-furylmethylsulfinyl)acetamide,
N-{4-[4-(piperidinomethyl)pyridyl-2-oxy]-2-butenyl}-2-(3-furylmethylsulfonyl)acetamide,
N-{4-[4-(piperidinomethyl)pyridyl-2-oxy]-2-butenyl}-2-(3-furylmethylsulfonyl)acetamide,
N-{4-[4-(dimethylaminomethyl)pyridyl-2-oxy]-2-butenyl}-2-(furfurylthio)acetamide,
N-{4-[4-(dimethylaminomethyl)pyridyl-2-oxy]-2-butenyl}-2-(furfurylsulfinyl)acetamide,
N-{4-[4-(dimethylaminomethyl)pyridyl-2-oxy]-2-butenyl}-2-(furfurylsulfonyl)acetamide,
N-{4-[4-(dimethylaminomethyl)pyridyl-2-oxy]-2-butenyl}-2-(3-furylmethylthio)acetamide,
N-{4-[4-(dimethylaminomethyl)pyridyl-2-oxy]-2-butenyl}-2-(3-furylmethylsulfinyl)acetamide,
N-{4-[4-(dimethylaminomethyl)pyridyl-2-oxy]-2-butenyl}-2-(3-furylmethylsulfonyl)acetamide,
N-{4-[4-(3-methylpiperidinomethyl)pyridyl-2-oxy]-2-butenyl}-2-(furfurylthio)acetamide,
N-{4-[4-(3-methylpiperidinomethyl)pyridyl-2-oxy]-2-butenyl}-2-(furfurylsulfonyl)acetamide,
N-{4-[4-(3-methylpiperidinomethyl)pyridyl-2-oxy]-2-butenyl}-2-(furfurylsulfonyl)acetamide,
N-{4-[4-(3-methylpiperidinomethyl)pyridyl-2-oxy]-2-butenyl}-2-(3-furylmethylthio)acetamide,
N-{4-[4-(3-methylpiperidinomethyl)pyridyl-2-oxy]-2-butenyl}-2-(3-furylmethylsulfinyl)acetamide,
N-{4-[4-(3-methylpiperidinomethyl)pyridyl-2-oxy]-2-butenyl}-2-(3-furylmethylsulfonyl)acetamide,
N-{4-[4-(pyrrolidinomethyl)pyridyl-2-oxy]-2-butenyl}-2-(furfurylthio)acetamide,
N-{4-[4-(pyrrolidinomethyl)pyridyl-2-oxy]-2-butenyl}-2-(furfurylsulfinyl)acetamide,
N-{4-[4-(pyrrolidinomethyl)pyridyl-2-oxy]-2-butenyl}-2-(furfurylsulfonyl)acetamide,
N-{4-[4-(pyrrolidinomethyl)pyridyl-2-oxy]-2-butenyl}-2-(3-furylmethylthio)acetamide,
N-{4-[4-(pyrrolidinomethyl)pyridyl-2-oxy]-2-butenyl}-2-(3-furylmethylsulfinyl)acetamide,
N-{4-[4-(pyrrolidinomethyl)pyridyl-2-oxy]-2-butenyl}-2-(3-furylmethylsulfonyl)acetamide,
N-{4-[4-(morpholinomethyl)pyridyl-2-oxy]-2-butenyl}-2-(furfurylthio)acetamide,
N-{4-[4-(morpholinomethyl)pyridyl-2-oxy]-2-butenyl}-2-(furfurylsulfinyl)acetamide,
N-{4-[4-(morpholinomethyl)pyridyl-2-oxy]-2-butenyl}-2-(furfurylsulfonyl)acetamide,
N-{4-[4-(morpholinomethyl)pyridyl-2-oxy]-2-butenyl}-2-(3-furylmethylthio)acetamide,
N-{4-[4-(morpholinomethyl)pyridyl-2-oxy]-2-butenyl}-2-(3-furylmethylsulfinyl)acetamide,
N-{4-[4-(morpholinomethyl)pyridyl-2-oxy]-2-butenyl}-2-(3-furylmethylsulfonyl)acetamide,
N-{4-[4-(1,2,3 6-tetrahydro-1-pyridylmethyl)pyridyl-2-oxy]-2-butenyl}-2-(furfurylthio)acetamide,
N-{4-[4-(1,2,3 6-tetrahydro-1-pyridylmethyl)pyridyl-2-oxy]-2-butenyl}-2-(furfurylthio)acetamide,
N-{4-[4-(1,2,3 6-tetrahydro-1-pyridylmethyl)pyridyl-2-oxy]-2-butenyl}-2-(furfurylsulfinyl)acetamide,
N-{4-[4-(1,2,3 6-tetrahydro-1-pyridylmethyl)pyridyl-2-oxy]-2-butenyl}-2-(furfurylsulfonyl)acetamide,
N-{4-[4-(1,2,3 6-tetrahydro-1-pyridylmethyl)pyridyl-2-oxy]-2-butenyl}-2-(3-furylmethylthio)acetamide,
N-{4-[4-(1,2,3 6-tetrahydro-1-pyridylmethyl)pyridyl-2-oxy]-2-butenyl}-2-(3-furylmethylsulfinyl)acetamide,
N-{4-[4-(1,2,3 6-tetrahydro-1-pyridylmethyl)pyridyl-2-oxy]-2-butenyl}-2-(3-furylmethylsulfonyl)acetamide,
N-{4-[4-(1-perhydroazepinylmethyl)pyridyl-2-oxy]-2-butenyl}-2-(furfurylthio)acetamide,
N-{4-[4-(1-perhydroazepinylmethyl)pyridyl-2-oxy]-2-butenyl}-2-(furfurylsulfinyl)acetamide,
N-{4-[4-(1-perhydroazepinylmethyl)pyridyl-2-oxy]-2-butenyl}-2-(furfurylsulfonyl)acetamide,
N-{4-[4-(1-perhydroazepinylmethyl)pyridyl-2-oxy]-2-butenyl}-2-(3-furylmethylthio)acetamide,
N-{4-[4-(1-perhydroazepinylmethyl)pyridyl-2-oxy]-2-butenyl}-2-(3-furylmethylsulfinyl)acetamide,
N-{4-[4-(1-perhydroazepinylmethyl)pyridyl-2-oxy]-2-butenyl}-2-(3-furylmethylsulfonyl)acetamide,
N-{4-[4-(4-methyl-1-piperazinylmethyl)pyridyl-2-oxy]-2-butenyl}-2-(furfurylthio)acetamide,
N-{4-[4-(4-methyl-1-piperazinylmethyl)pyridyl-2-oxy]-2-butenyl}-2-(furfurylsufinyl)acetamide,
N-{4-[4-(4-methyl-1-piperazinylmethyl)pyridyl-2-oxy]-2-butenyl}-2-(furfurylsulfonyl)acetamide,
N-{4-[4-(4-methyl-1-piperazinylmethyl)pyridyl-2-oxy]-2-butenyl}-2-(3-furylmethylthio)acetamide,
N-{4-[4-(4-methyl-1-piperazinylmethyl)pyridyl-2-oxy]-2-butenyl}-2-(3-furylmethylsulfinyl)acetamide,
N-{4-[4-(4-methyl-1-piperazinylmethyl)pyridyl-2-oxy]-2-butenyl}-2-(3-furylmethylsulfonyl)acetamide,
N-{4-[4-(thiomorpholinomethyl)pyridyl-2-oxy]-2butenyl}-2-(furfurylthio)acetamide,
N-{4-[4-(thiomorpholinomethyl)pyridyl-2-oxy]-2butenyl}-2-(furfurylsulfinyl)acetamide,
N-{4-[4-(thiomorpholinomethyl)pyridyl-2-oxy]-2butenyl}-(furfurylsulfonyl)acetamide,
N-{4-[4-(thiomorpholinomethyl)pyridyl-2-oxy]-2butenyl}-2-(3-furylmethylthio)acetamide,
N-{4-[4-(thiomorpholinomethyl)pyridyl-2-oxy]-2butenyl}-2-(3-furfurylmethylsulfinyl)acetamide,
N-{4-[4-(thiomorpholinomethyl)pyridyl-2-oxy]-2butenyl}-2-(3-furylmethylsulfonyl)acetamide,
N-{4-[4-(4-hydroxypiperidinomethyl)pyridyl-2-oxy]-2-butenyl}-2-(furfurylthio)acetamide,
N-{4-[4-(4-hydroxypiperidinomethyl)pyridyl-2-oxy]-2-butenyl}-2-(furfurylsulfinyl)acetamide,
N-{4-[4-(4-hydroxypiperidinomethyl)pyridyl-2-oxy]-2-butenyl}-2-(furfurylsulfonyl)acetamide,
N-{4-[4-(4-hydroxypiperidinomethyl)pyridyl-2-oxy]-2-butenyl}-2-(3-furylmethylthio)acetamide,
N-{4-[4-(4-hydroxypiperidinomethyl)pyridyl-2-oxy]-2-butenyl}-2-(3-furylmethylsulfinyl)acetamide,
N-{4-[4-(4-hydroxypiperidinomethyl)pyridyl-2-oxy]-2-butenyl}-2-(3-furylmethylsulfonyl)acetamide,
N-{4-[4-(piperidinomethyl)pyridyl-2-oxy]butyl}-2-(furfurylthio)acetamide, N-{4-[4-(piperidinomethyl)pyridyl-2-oxy]butyl}-2-(furfurylsulfinyl)acetamide,
N-{4-[4-(piperidinomethyl)pyridyl-2-oxy]butyl}-2-(furfurylsulfonyl)acetamide,
N-{4-[4-(piperidinomethyl)pyridyl-2-oxy]butyl}-2-(3-furylmethylthio)acetamide,
N-{4-[4-(piperidinomethyl)pyridyl-2-oxy]butyl}-2-(3-furylmethylsulfinyl)acetamide,
N-{4-[4-(piperidinomethyl)pyridyl-2-oxy]butyl}-2-(3-furylmethylsulfonyl)acetamide,
N-{4-[4-(dimethylaminomethyl)pyridyl-2-oxy]butyl}-2-(furfurylthio)acetamide,
N-{4-[4-(dimethylaminomethyl)pyridyl-2-oxy]butyl}-2-(furfurylsulfinyl)acetamide,
N-{4-[4-(dimethylaminomethyl)pyridyl-2-oxy]butyl}-2-(furfurylsulfonyl)acetamide,
N-{4-[4-(dimethylaminomethyl)pyridyl-2-oxy]butyl}-2-(3-furylmethylthio)acetamide,
N-{4-[4-(dimethylaminomethyl)pyridyl-2-oxy]butyl}-2-(3-furylmethylsulfinyl)acetamide,
N-{4-[4-(dimethylaminomethyl)pyridyl-2-oxy]butyl}-2-(3-furylmethylsulfonyl)acetamide,
N-{4-[4-(4-methyl-1-piperazinylmethyl)pyridyl-2-oxy]-butyl}2-(furfurylthio)acetamide,
N-{4-[4-(4-methyl-1-piperazinylmethyl)pyridyl-2-oxy]-butyl}2-(furfurylsulfinyl)acetamide,
N-{4-[4-(4-methyl-1-piperazinylmethyl)pyridyl-2-oxy]-butyl}2-(furfurylsulfonyl)acetamide,
N-{4-[4-(4-methyl-1-piperazinylmethyl)pyridyl-2-oxy]-butyl}2-(3-furylmethylthio)acetamide,
N-{4-[4-(4-methyl-1-piperazinylmethyl)pyridyl-2-oxy]-butyl}2-(3-furylmethylsulfinyl)acetamide,
N-{4-[4-(4-methyl-1-piperazinylmethyl)pyridyl-2-oxy]-butyl}2-(3-furylmethylsulfonyl)acetamide,
N-{4-[4-(pyrrolidinomethyl)pyridyl-2-oxy]butyl}-2-(furfurylthio)acetamide,
N-{4-[4-(pyrrolidinomethyl)pyridyl-2-oxy]butyl}-2-(furfurylsulfinyl)acetamide,
N-{4-[4-(pyrrolidinomethyl)pyridyl-2-oxy]butyl}-2-(furfurylsulfonyl)acetamide,
N-{4-[4-(pyrrolidinomethyl)pyridyl-2-oxy]butyl}-2-(3-furylmethylthio)acetamide,
N-{4-[4-(pyrrolidinomethyl)pyridyl-2-oxy]butyl}-2-(3-furylmethylsulfinyl)acetamide, and
N-{4-[4-(pyrrolidinomethyl)pyridyl-2-oxy]butyl}-2-(3-furylmethylsulfonyl)acetamide.

Preferred among the above-illustrated compounds are
N-{4[4-(piperidinomethyl)pyridyl-2-oxy]-cis-2-butenyl}-2-(furfurylthio)acetamide,
N-{4[4-(piperidinomethyl)pyridyl-2-oxy]-cis-2-butenyl}-2-(furfurylsulfinyl)acetamide,
N-{4[4-(piperidinomethyl)pyridyl-2-oxy]-cis-2-butenyl}-2-(3-furfurylmethylsulfonyl)acetamide,
N-{4-[4-(dimethylaminomethyl)pyridyl-2-oxy]-cis-2-butenyl}-2-(furfurylsulfinyl)acetamide,
N-{4-[4-(3-methylpiperidinomethyl)pyridyl-2-oxy]-cis-2-butenyl}-2-(furfurylsulfinyl)acetamide,
N-{4-[4-(pyrrolidinomethyl)pyridyl-2-oxy]-cis-2-butenyl}-(furfurylsulfinyl)acetamide,
N-{4-[4-(morpholinomethyl)pyridyl-2-oxy]-cis-2-butenyl}-2-(furfurylsulfinyl)acetamide,
N-{4-[4-(1,2,3,6-tetrahydro-1-pyridylmethyl)pyridyl-2-oxy]-cis-2-butenyl}-2-(furfurylsulfinyl)acetamide, and
N-{4-[4-(piperidinomethyl)pyridyl-2-oxy]butyl}-2-(furfurylsulfinyl)acetamide.

Especially preferred compounds of formula (I) are

N-{4-[4-(piperidinomethyl)pyridyl-2-oxy]-cis-2-butenyl}-2-(furfurylsulfinyl)acetamide,
N-{4-[4-(piperidinomethyl)pyridyl-2-oxy]-cis-2-butenyl}-2-(3-furylmethylsulfonyl)acetamide, and
N-{4-[4-(piperidinomethyl)pyridyl-2-oxy]butyl}-2-(furfurylsulfinyl)acetamide.

The compound of this invention contains a basic amino group in the molecule, and can exist in the form of an acid addition salt. Examples of the acid addition salt are salts with inorganic acids such as hydrochloric acid, sulfuric acid, hydrobromic acid, hydriodic acid, nitric acid and phosphoric acid, and salts with organic acids such as lactic acid, maleic acid, fumaric acid, benzoic acid, salicyclic acid, tartaric acid, acetic acid, benzenesulfonic acid, carbonic acid, citric acid, gluconic acid, glutamic acid, mandelic acid, metasulfonic acid, panthotheic acid, stearic acid, succinic acid and tannic acid. Suitable salts are pharmaceutically acceptable salts.

The compound of formula (I) can be produced by reacting an amine compound represented by the following formula

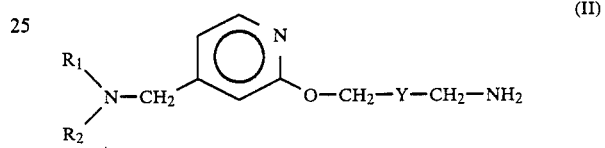

(II)

wherein $R_1$, $R_2$ and Y are as defined hereinabove, with an acetic acid derivative represented by the following formula

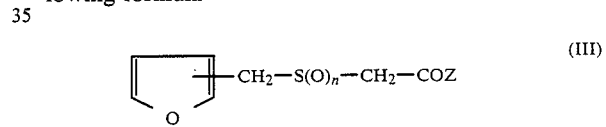

(III)

wherein Z represents a halogen atom or a hydroxyl group, and n is as defined hereinabove.

The reaction of the compound of formula (II) with the compound of formula (III) can be carried out by a known amidation reaction. Thus, the reaction of the amine compound (II) with the halide compound of formula (III) in which Z is a halogen atom may be carried out usually in the presence of a base in a reaction medium. Examples of the base are inorganic bases such as sodium hydroxide, potassium hydroxide, potassium carbonate and sodium carbonate, and organic bases such as pyridine and triethylamine. The reaction medium may generally be an organic solvent, for example a halogenated hydrocarbon such as dichloromethane and chloroform, an aromatic hydrocarbon such as benzene, toluene and xylene, an ether such as tetrahydrofuran and dioxane, an amide such as dimethylformamide and dimethylacetamide, acetonitrile, or dimethyl sulfoxide, either singly or in combination. The reaction temperature and pressure may be varied depending upon the starting compounds used. Usually, the reaction can be conveniently carried out under atmospheric pressure at a temperature of 0° C. to the refluxing temperature of the reaction mixture, preferably 0° C. to room temperature.

The reaction of the amine compound (II) with the carboxylic acid compound of formula (III) in which Z is a hydroxyl group is a dehydrocondensation reaction, and may be carried out usually in the presence of a dehydrocondensing agent in a reaction medium. The condensation agent may be, for example, dicyclohexylcarbodiimide (DCC) or 1-ethyl-3-(3-dimethylaminopropyl)-carbodiimide hydrochloride (WSC). The reaction medium is generally an inert solvent, for example, an aromatic hydrocaron such as benzene, toluene and xylene, an ether such as tetrahydrofuran and dioxane, an amide such as dimethylformamide and dimethylacetamide, acetonitrile, or dimethyl sulfoxide. The reaction temperature and pressure may be varied depending upon the starting compounds used. Usually, the reaction can be conveniently carried out under atmospheric pressure at a temperature of 0° C. to the refluxing temperature of the reaction mixture, preferably 0° C. to room temperature.

The carboxylic acid compound of formula (III) in which Z is a hydroxyl group may be reacted with the amine compound (II) after it is converted to an active ester, for example, by reacting it with N-hydroxylsuccinimide or 4-nitrophenol.

In the amidation reaction, the compound of formula (III) may be used in an amount of generally 1 to 5 moles, preferably 1.0 to 2.0 moles, per mole of the compound of formula (II).

The amine compound (II) used as one starting material in the amidation reaction is known per se, or may be produced by a known method (see, for example, European Patent No. 177016 cited hereinabove. Examples of the amine compound (II) include 4-[4-(piperidinomethyl)pyridyl-2-oxy]-2-butenamine,
4-[4-(dimethylaminomethyl)pyridyl-2-oxy]-2-butenamine,
4-[4-(3-methylpiperidinomethyl)pyridyl-2-oxy]-2-butenamine,
4-[4-(pyrrolidinomethyl)pyridyl-2-oxy]-2-butenamine,
4-[4-(morpholinometyl)pyridyl-2-oxy]-2-butenamine,
4-[4-(1,2,3,6-tetrahydro-1-pyridylmethyl)pyridyl-2-oxy]-2-butenamine,
4-[4-(1-perhydroazepinylmethyl)pyridyl-2-oxy]-2-butenamine,
4-[4-(4-methyl-1-piperazinylmethyl)pyridyl-2-oxy]-2-butenamine,
4-[4-(4-hydroxypiperidinomethyl)pyridyl-2-oxy]-2-butenamine,
4-[4-(thiomorpholinomethyl)pyridyl-2-oxy]-2-butenamine,
4-[4-(piperidinomethyl)pyridyl-2-oxy]butanamine,
4-[4-(dimethylaminomethyl)pyridyl-2-oxy]butanamine,
4-[4-(3-methylpiperidinomethyl)pyridyl-2-oxy]butanamine,
4-[4-(pyrrolidinomethyl)pyridyl-2-oxy]butanamine,
4-[4-(morpholinomethyl)pyridyl-2-oxy]butanamine,
4-[4-(1,2,3,6-tetrahydro-1-pyridylmethyl)pyridyl-2-oxy]butanamine,
4-[4-(1-perhydroazepinylmethyl)pyridyl-2-oxy]butanamine,
4-[4-(4-methyl-1-piperazinylmethyl)pyridyl-2-oxy]butanamine,
4-[4-(4-hydroxypiperidinomethyl)pyridyl-2-oxy]butanamine, and
4-[4-(thiomorpholinomethyl)pyridyl-2-oxy]butanamine.

The acetic acid derivative of formula (III) may be obtained by reacting the corresponding furylmethylmercaptan with a haloacetate ester, if desired oxidizing the reaction product, and hydrolyzing it (see Japanese Laid-Open Patent Publication No. 153268/1987). Examples include 2-(furfurylthio)acetic acid, 2-(furfurylsulfinyl)acetic acid, 2-(furfurylsulfonyl)acetic acid, 2-(3-furylmethylthio)acetic acid, 2-(3-furylmethylsulfinyl)acetic acid and 2-(3-furylmethylsulfonyl)acetic acid.

The compound of formula (I) may also be produced through the route shown by the following reaction scheme A.

Reaction Scheme A

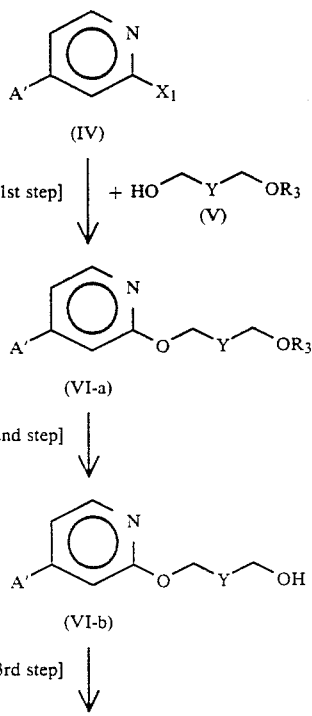

-continued
Reaction Scheme A
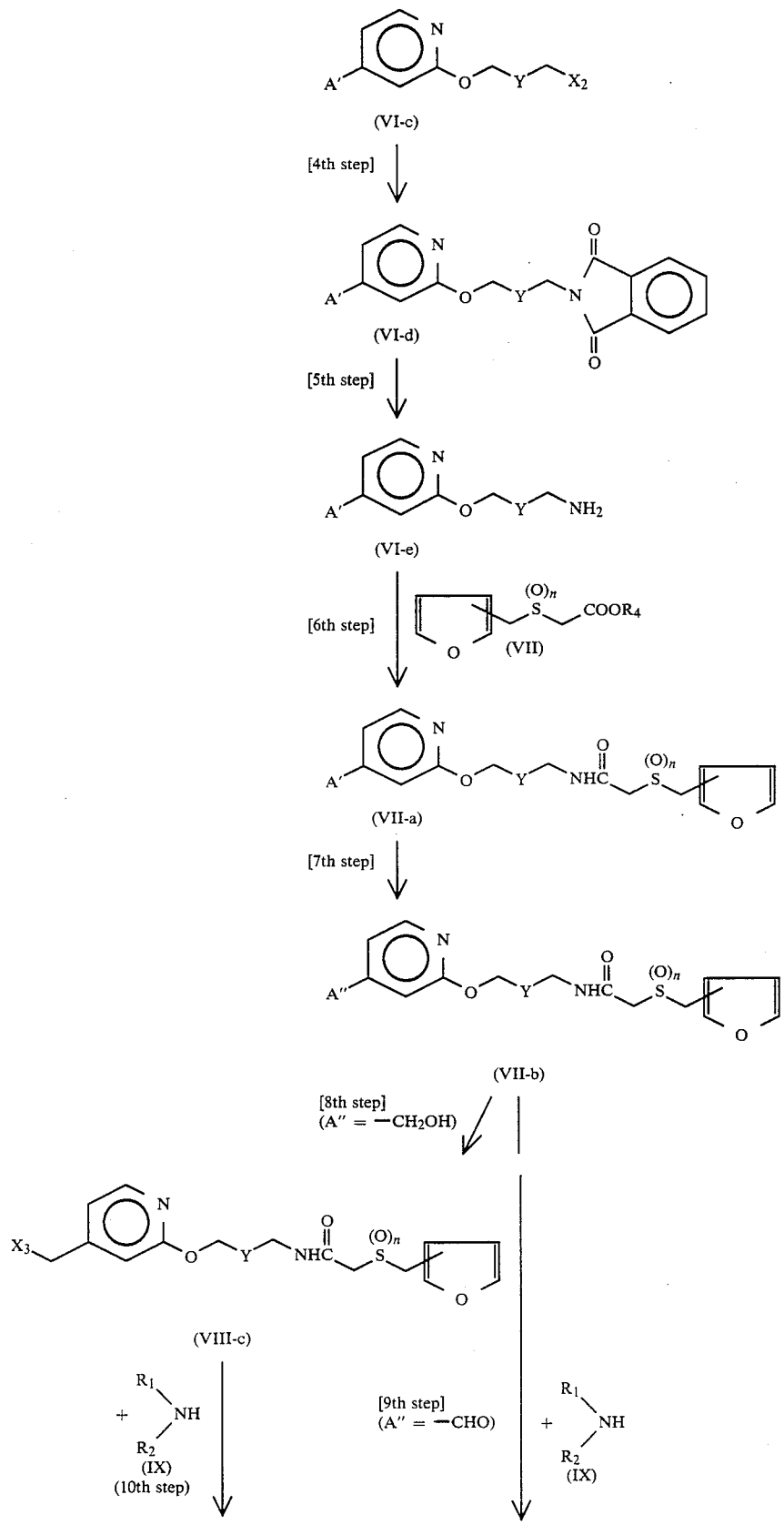

-continued
Reaction Scheme A

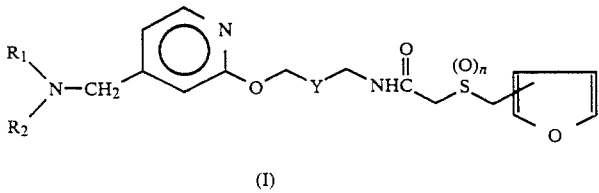

(I)

In the above formulae:

A' is a protected formyl group or a hydroxymethyl group in which the hydroxyl group is protected;
A" is a formyl or hydroxymethyl group;
$R_3$ is a protective group for the hydroxyl group;
$R_4$ is an active ester residue, such as an o- or p-nitrophenyl group or a 2,4-dinitrophenyl group;
$X_1$, $X_2$ and $X_3$ each represent a halogen atom; and
$R_1$, $R_2$, Y and n are as defined above.

The steps shown in the Reaction Scheme A will now be described more specifically.

First Step

In this step, a halogenopyridine derivative of formula (IV) is reacted with an alcohol derivative of formula (V) to produce a pyridyl ether derivative of formula (VI-a).

In the starting halogenopyridine derivative of general formula (IV), the halogen atom (Xl) is preferably a bromine or chlorine atom. The halogenopyridine derivative may be produced in accordance with the following Reaction Scheme B.

The "protected formyl group", as used herein, includes, for example, cyclic acetals such as 2-(1,3-dioxolane), 2-(1,3-dioxane), 2-(1,3-oxathilane) and 2-(1,3-dioxathiane) and acyclic acetals such as dimethylacetal, diethylacetal and dipropylacetal. The protected formyl group may be formed, for example, by reacting the formyl group with an alcohol or an orthoformate ester. Examples of alcohols that can be used to protect the formyl group are lower alcohols such as methanol, ethanol, and propanol, and lower alkylene glycols such as 1,2-ethylene glycol and 1,3-propylene glycol. The orthoformate ester may be, for example, a lower alkyl ester of orthoformic acid such as methyl orthoformate or ethyl orthoformate.

The protective group of the hydroxyl group may be ordinary protective groups for the hydroxyl group which can be easily split off by hydrolysis. Examples include a tetrahydropyranyl group, lower alkoxyalkyl groups such as methoxymethyl and methoxyethyl groups, aralkyl groups such as triphenylmethyl and diphenylmethyl groups and silyl groups such as a tri- Reaction Scheme B

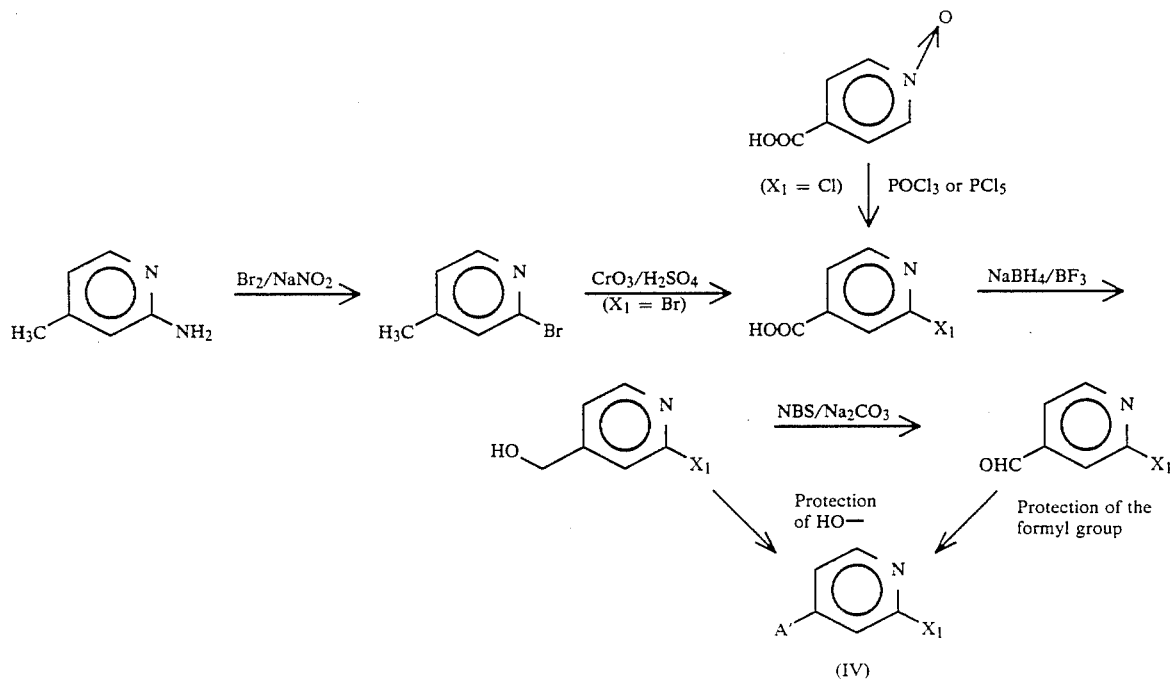

Specifically, it may be produced by reacting 2-amino-4-methylpyridine or isonicotinic acid N-oxide, which is easily available industrially, with the reagents indicated in the above Reaction Scheme B (for details, see Referential Examples 2 to 10 given hereinbelow).

methylsilyl group.

Examples of the alcohol derivative of formula (V) are 4-(2-tetrahydropyranyloxy)-2-buten-1-ol, 4-(triphenylmethyloxy)-2-buten-1-ol, 4-benzyloxy-2-buten-1-ol, 4-(2-tetrahydrofuryl)-2-buten-1-ol, 4-(2-tetrahydropyranyloxy)-butan-1-ol, 4-(triphenylmethyloxy)-butan-1-ol, 4-(benzyloxy)-butan-1-ol, and 4-(2-tetrahydrofuryl)-butan-1-ol.

The reaction of the halogenopyridine derivative of formula (IV) with the alcohol derivative of formula (V) may be carried out by method (a) or (b) described below.

[Method (a)]

This method is carried out in the presence of a phase transfer catalyst and an inorganic base. Preferably, the phase transfer catalyst may be, for example, an organic ammonium salt or a crown ether. Examples of the organic ammonium salt are tetra-n-butyl ammonium iodide, tetra-n-butyl ammonium bromide, tetra-n-butyl ammonium chloride, tetra-n-butyl ammonium hydrogen sulfate. Examples of the crown ether are 12-crown-4 and 18-crown-6. The inorganic base may be, for example, an alkali metal hydroxide or carbonate such as sodium hydroxide, potassium hydroxide, sodium carbonate, potassium carbonate.

The amount of each of the phase transfer catalyst and the inorganic base is suitably 1/10 to 2 equivalents based on the compound of formula (V).

The reaction is desirably carried out usually in a solvent. Examples of suitable solvents are aromatic hydrocarbons such as benzene, toluene and xylene, ethers such as dimethoxyethane, tetrahydrofuran and dioxane, amides such as dimethylformamide and nitriles such as acetonitrile and propionitrile.

Preferably, the reaction temperature is generally in the range of 80° to 200° C.

[Method (b)]

This method is carried out by reacting the compound of formula (IV) with the compound of formula (V) in the presence of an alkali metal compound in the solvent described above. Examples of the alkali metal compound are sodium hydride, potassium hydride and sodiumamide. Preferably, the amount of the alkali metal compound used is generally 1 to 3 equivalents based on the compound of formula (V). The reaction may be carried out at a temperature of usually about 35° to 120° C.

In both the methods (a) and (b), the compound of formula (V) may be used in a proportion of generally 1 to 3 moles, preferably 1.0 to 1.5 moles, per mole of the compound of formula (IV).

Second Step

In this step, the pyridyl ether derivative of formula (VI-a) formed in the first step is hydrolyzed to give a pyridyloxy alcohol derivative of formula (VI-b).

Preferably, this step is carried out in the presence of an acid such as hydrochloric acid, sulfuric acid, acetic acid, p-toluenesulfonic acid, camphorsulfonic acid or citric acid; or pyridinium p-toluenesulfonate or pyridinium chloride.

Desirably, the hydrolysis is carried out usually in water or a mixture of it with a water-miscible organic solvent such as acetone, or an alcohol (e.g., methanol, ethanol or propanol). The reaction smoothly proceeds usually at a temperature of about 25° to 70° C.

Third Step

This step comprises reacting the pyridineoxy alcohol derivative of formula (VI-b) obtained in the second step with a halogenating agent to produce a pyridyloxyhalogen derivative of formula (VI-c).

Example of the halogenating agent that can be used in this step include thionyl chloride, p-toluenesulfonyl chloride, methanesulfonyl chloride, phosphorus oxychloride, phosphorus trichloride, phosphorus pentabromide, phosphorus tribromide, phosphorus oxybromide, methanesulfonic anhydride, and methanesulfonyl bromide. The halogenating agent may be used usually in a proportion of 1 to 5 equivalents, preferably 1 to 2 equivalents, per mole of the pyridyloxyalcohol derivative of formula (VI-b).

Preferably, this step is carried out in the presence of a base, for example, an organic base such as triethylamine or pyridine, or an inorganic base such as anhydrous potassium carbonate or anhydrous sodium hydrogen carbonate. The amount of the base is preferably 1 to 2 equivalents based on the halogenating agent.

Desirably, the reaction is carried out in a solvent. Examples of suitable solvents are halogenated hydrocarbons such as chloroform and dichloromethane, aromatic hydrocarbons such as benzene and toluene, and ethers such as tetrahydrofuran and dimethoxyethane. The reaction proceeds smoothly at a temperature of generally from about $-10°$ C. to about 15° C.

Fourth Step

In this step, a pyridyloxyphthalimide derivative of general formula (VI-d) is produced by reacting the pyridyloxyhalogen derivative (VI-c) formed in the third step with phthalimide or its alkali metal salt.

When phthalimide is used, the reaction in this step may be carried out in the same way as in method (a) in the first step described hereinabove. When the alkali metal salt of phthalimide is used, the reaction is carried out in the same way as in method (a) except that the use of the inorganic base in method (a) is omitted.

Fifth Step

In this step, the pyridyloxyphthalimide derivative of formula (VI-d) formed in the fourth step is hydrolyzed to produce a pyridyloxyamine derivatives of formula (VI-d).

Preferably, the reaction in this step is carried out in the presence of an inorganic base such as hydrazine, sodium hydroxide, potassium hydroxide, sodium carbonate or potassium carbonate, or an organic base such as methylamine and ethylamine. Desirably, the amount of the base is usually 1 to 2 equivalents per mole of the pyridyloxyphthalimide derivative of formula (VI-d).

The reaction carried out desirably in a solvent, for example an alcohol such as methanol, ethanol, propanol, water, or an ether such as ethyl ether, tetrahydrofuran or dimethoxyethane. The reaction proceeds smoothly generally at a temperature of 30° to 100° C.

The compounds of formulae (VI-a), (VI-b), (VI-c), (VI-d) and (VI-e) obtained in the first to the fifth steps may, if desired, be converted to the corresponding compounds having a formyl or hydroxymethyl group by treating them with acids such as mineral acids (e.g., hydrochloric acid or sulfuric acid) or organic acids (e.g., acetic acid, p-toluenesulfonic acid, camphorsulfonic acid and citric acid) to deprotect them.

Sixth Step

In this step, the pyridyloxyamine of formula (VI-e) obtained in the fifth step is reacted with a furfurylthio ester of general formula (VII) to produce an acetal pyridyloxy derivative represented by general formula (VIII-a).

The proportion of the compound of formula (VII) relative to the compound of formula (VI-e) is not critical, but the compound of formula (VII) is suitably used in a proportion of 1 to 5 moles, perferably 1 to 2 moles, per mole of the compound of formula (VI-e).

The furfurylthio ester of formula (VII) to be reacted with the compound of formula (VI-e) in this step may be obtained, for example, by reacting 2-(furfurylsulfinyl)acetic acid with a nitrophenol (e.g., p-nitrophenol, 2,4-dinitrophenol, or o-nitrophenol) in the presence of a dehydrocondensing agent (such as dicyclohexylcarbodiimide).

The active ester residue (R$_4$) is preferably the o- or p-nitrophenyl group or the 2,4-dinitrophenyl group mentioned above. It may be another active ester residue usually employed in amidization in the field of peptide chemistry, for example residues of N-hydroxysuccinimide, pentachlorophenol, pentafluorophenol, N-hydroxyphthalimide and N-hydroxy-5-norbornene-2,3-dicarboximide.

The above reaction is desirably carried out in a solvent, for example, an ether such as ethyl ether, tetrahydrofuran, dimethoxyethane or dioxane, a halogenated hydrocarbon such as chloroform or dichloromethane, an aromatic hydrocarbon such as benzene and toluene, or an amide such as dimethylformamide.

The reaction proceeds smoothly usually at a temperature of about 0° to 50° C.

Seventh Step

In this step, the acetalpyridyloxy derivative of formula (VIII-a) obtained in the sixth step is deprotected to produce a pyridyloxy derivative of formula (VIII-b).

Desirably, this step is carried out in the presence of an acid. Suitable acids used for this purpose include, for example, mineral acids such as hydrochloric acid and sulfuric acid and organic acids such as p-toluenesulfonic acid, camphorsulfonic acid and citric acid. The amount of the acid used is generally 1 to 5 equivalents per mole of the compound of formula (VIII-a).

Desirably, this reaction is carried out in a solvent, for example water, a ketone such as acetone, an alcohol such as methanol, ethanol and propanol, an ether such as tetrahydrofuran and dimethoxyethane, or a nitrile such as acetonitrile, either singly or in combination. The reaction can be carried out generally at room temperature to about 120° C., optionally under heating at a temperature of about 70° to 120° C.

Eighth Step

In this step, the pyridyloxy derivative of formula (VIII-b) in which A" is a hydroxymethyl group obtained in the seventh step is reacted with a halogenating agent to produce a pyridyloxy derivative of formula (VIII-c).

Examples of the halogenating agent used in this step are thionyl chloride, p-toluenesulfonyl chloride, methanesulfonyl chloride, phosphorus oxychloride, phosphorus pentachloride, phosphorus trichloride, methanesulfonic anhydride, phosphorus tribromide and methanesulfonyl bromide. The halogenating agent may be used in a proportion of generally 1 to 5 equivalents, preferably 1 to 2 equivalents, per mole of the compound of formula (VIII-b).

Preferably, this step is carried out usually in the presence of base. Examples of the base include organic bases such as triethylamine and pyridine and inorganic bases such as potassium carbonate, sodium carbonate and sodium hydrogen carbonate. The amount of the base used is generally at least equal in equivalent weight to the halogenating agent, preferably 1 to 1.5 equivalents basd on the latter. The halogenation reaction is desirably carried out in a solvent, for example a halogenated hydrocarbon such as chloroform or dichloromethane, an aromatic hydrocarbon such as benzene and toluene, or an ether such as tetrahydrofuran and dimethoxyethane. The reaction proceeds smoothly usually at a temperature of −10° to about 15° C.

If required, the pyridyloxy derivative of formula (VIII-c) produced in this step may be directly used in the subsequent reaction without isolation.

Ninth Step

In this step, the compound of formula (VIII-b) in which A" is a formyl group obtained in the seventh step, i.e. a compound of the following formula

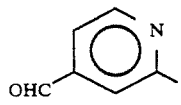 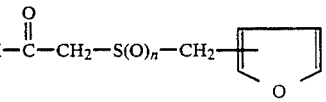

(VIII-d)

wherein Y and n are as defined above, is reacted with a disubstituted amine of formula (IX) to produce the compound of formula (I).

This step is carried out by using a reducing agent. Examples of the reducing agent are metal hydride complexes such as sodium borohydride, lithium borohydride, and sodium cyanoborohydride. The reaction is desirably carried out in a solvent, for example a halogenated hydrocarbon such as chloroform and dichloromethane, or a lower alcohol such as methanol, ethanol and isopropanol. The reaction usually proceeds smoothly at a temperature of −10° C. to 15° C.

Tenth Step

In this step, the compound of formula (VIII-c) obtained in the eighth step, i.e. a compound of the following formula

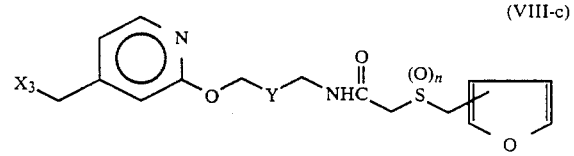

(VIII-c)

wherein Y, X$_3$ and n are as defined hereinabove, is reacted with the disubstituted amine of formula (IX) to produce the compound of formula (I).

This reaction is desirably carried out in a solvent, for example a halogenated hydrocarbon as chloroform and dichloromethane, a lower alcohol such as methanol, ethanol and isopropanol, or an ether such as tetrahydrofuran. The reaction is conveniently carried out usually at a temperature of 10° to 100° C., preferably at the refluxing temperature of the solvent. The suitable amount of the disubstituted amine of formula (IX) is generally 1 to 5 moles, preferably 2 to 4 moles, per mole of the compound of formula (VIII-c).

The compounds of formulae (VI-a), (VI-b), (VI-c), (VI-d) and (VI-e) in the Reaction Scheme A and the corresponding deprotected compounds resulting from conversion of the protected formyl group into the formyl group, namely the compounds of the following formula

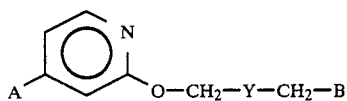

(VI)

wherein A represents a formyl group, a protected formyl group, a hydroxymethyl group or a hydroxymethyl group in which the hydroxyl group is protected, B represents a halogen atom, an amino group, a phthalimide group, a hydroxyl group or a protected hydroxyl group, and Y is as defined hereinabove, are novel compounds which are important intermediates for the compounds of formula (I).

The compounds of formulae (VIII-a), (VIII-b) and (VIII-c) in the Reaction Schme A, namely the compounds of the following formula

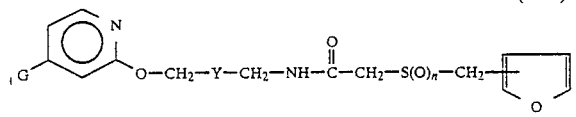

(VIII)

wherein G represents a formyl group, a protected formyl group, a hydroxymethyl group, a hydroxymethyl group having the hydroxyl group protected, or a halogenomethyl group, and Y and n are as defined hereinabove, are also novel compounds which are important intermediates of the production of the compounds of formula (I).

The compound of formula (I) in which n is 0 which is produced as above may be converted by oxidation into the corresponding compound of formula (I) in which n is 1.

The oxidation may be carried out by a conventional method in a solvent stable to oxidation using an oxidizing agent, for example hydrogen peroxide, t-butyl hydroperoxide, peroxy acids such as peroxyacetic acid, peroxybenzoic acid, m-chloroperoxybenzoic acid and peroxycamphor acid, sodium metaperoxyiodate, hydroperoxide, ozone, selenium dioxide, chromic acid, nitrogen tetroxide, iodine, bromine, N-bromosuccinimide, iodosyl benzene, sulfuryl chloride and t-butyl hypochlorite.

The compound of formula (I) produced as above may be isolated and purified by known methods such as crystallization, extraction and chromatography.

The compound of formula (I) may be converted to its acid addition salt by treatment with the aforesaid inorganic acids or organic acids in a customary manner.

The pyridyloxy derivative of formula (I) provided by this invention has gastric acid secretion inhibiting activity based on its excellent histamine $H_2$ receptor antagonizing activity, and an action of protecting the mucosa of the digestive organs, and can be used as an anti-peptic ulcer agent.

The excellent pharmacological activities of the compounds (I) of this invention can be demonstrated by the following standard animal experiments.

Test on histamine $H_2$ receptor antagonizing activity

Hartley-strain guinea pigs (male 300 to 350 g) were stunned with a blow to the head. The heart was removed, and the right atrium was dissected from the hearts in the Krebs' solution bubbled with a 95 % $O_2$ was suspended in an Organ bath filled with the Krebs' solution kept at 32° C. The gaseous mixture was passed through the Organ bath, and a diastolic tension was adjusted to 1 g. The contraction of the atrium was recorded by a force displacement transducer, and the heart rate was measured by interlocking a heart rate meter to the transducer.

Histamine (used in the form of dihydrochloride; the same hereinafter) was added to the Organ bath cumulatively in a concentration of $1\times10^{-8}$ M to $3\times10^{-5}$ M. Thus, the dose-response curve of histamine was obtained. The Organ bath was washed several times, and each of the test compounds ($1\times10^{-6}$, $1\times10^{-7}$ M) was added to the Organ bath, and a dose-response curve of histamine in the presence of the test compound was obtained 10 minutes later.

The $pA_2$ value of each of the test compound was determined from the first histamine dose-response curve and the histamine dose-response curve obtained in the presence of the test compounds by the method of J. M. Van Rossum (Arch. Int. Pharmacodyn. Ther., 143–299, 1963).

The results are shown in Table 1.

TABLE 1

| Test compound | $pA_2$ |
|---|---|
| Compound of Example 10 | 6.9 |
| Compound of Example 11 | 7.0 |
| Compound of Example 12 | 6.6 |

For comparison, cimetidine was used, and its $pA_2$, measured by the same procedure as above, was 6.5.

Test on the Action of Inhibiting Gastric Secretion Stimulated by Tetragastrin

This test was conducted by a partially modified version of the method of Ghosh et al. [M. N. Ghosh, H. O. Schild, Brit. J. Pharmacol., 13, 54–61 (1958)].

Male Wistar rats (body weight 200 to 250 g) which had been caused to fast for 24 hours were anesthetized by injecting urethane (1.4 g/kg) intraperitoneally.

Then, the pyrolus of the stomach was ligated, and a cannula was inserted into the esophagus and the fore-stomach portion. After fixation, physiological saline containing 1/2000N NaOH and kept at 37°±1° C. was perfused at a rate of 1 ml/min. by means of a peristaltic pump. The pH of the solution flowing from the cannula inserted in the fore-stomach portion was continuously recorded by a pH meter.

Tetragastrin (40 μg/kg/hr) was infused intravenously from a cannula injected in the caudal vein. After the increase of gastric acid secretion became constant (pH 3 to 4), each of the following compounds was administered through another caudal vein cannula, and its effect was examined.

The doses which evidently showed the action of inhibiting gastric acid secretion were evaluated on the following standards, and the efficacies are shown in Table 2.

| mg/kg, i.v. | Efficacy |
| --- | --- |
| 3–10 | + |
| 1–3 | ++ |
| 0.3–1 | +++ |
| 0.1–0.3 | ++++ |

TABLE 2

| Test compound | Efficacy |
| --- | --- |
| Compound of Example 1 | ++ |
| Compound of Example 2 | ++++ |
| Compound of Example 3 | +++ |
| Compound of Example 4 | +++ |
| Compound of Example 8 | +++ |
| Compound of Example 9 | ++ |
| Compound of Example 10 | +++ |
| Compound of Example 11 | ++ |
| Compound of Example 12 | ++ |
| Compound of Example 13 | +++ |
| Compound of Example 14 | ++ |
| Compound of Example 15 | ++ |
| Compound of Example 21 | ++++ |
| Compound of Example 22 | ++ |
| Cimetidine | + |

Test on the Action of Gastric Mucosal Protection

Male Donryu rats (150 to 250 g) which had been caused to fast for 24 hours were used. In the test, a necrotizing agent (0.4N HCl+50% ethanol) was orally administered in a dose of 5 ml/kg 30 minutes after administering each of the test compounds (10 mg/kg, p.o.). One hour after administration of the necrotizing agent, the stomach was isolated and fixed by formalin. The area of a lesion was measured, and by comparison with a control group, the percent inhibition was determined. The results are shown in Table 3.

TABLE 3

| Test compound | Inhibition (%) |
| --- | --- |
| Compound of Example 1 | 66 |
| Compound of Example 2 | 32 |
| Compound of Example 3 | 62 |
| Compound of Example 12 | 38 |
| Compound of Example 21 | 32 |

The data obtained by the above pharmacological test demonstrate that the compounds of formula (I) provided by this invention have strong histamine $H_2$ receptor antagonizing activity and gastric acid secretion inhibiting activity, and also an excellent action of gastric mucosal protection. Accordingly, they are useful as drugs for therapy or treatment of gastric ulcer or duodenal ulcer.

The compound of formula (I) provided by this invention can be administered orally or parenterally (for example, intramuscularly, intravenously, subcutaneously, or intrarectally) to humans and other mammals for the treatment or prevention of diseases, particularly gastric ulcer or duodenal ulcer.

For use as medicaments, the compound of formula (I) may be formulated by known methods (see Remington, "Pharmaceutical Sciences", Mack Publishing Company, Easton, Pa., U. S. A., 14th edition, 1970) into various forms suitable for oral or parenteral administration. For example, the compound of this invention can be formulated by using various nontoxic carriers or diluents normally used in drugs of this type, for example vehicles, binders, lubricants, disintegrants, antiseptics, isotonizing agents, stabilizers, dispersants, antioxidants, coloring agents, flavoring agents, buffers, propellants and surface-active agents.

Depending upon their uses, such medicaments may be formulated into tablets, capsules, granules, powders, pellets, pills, trouches, suppositories, injectable preparations, syrups, and aerosols. Specific examples of the nontoxic carriers or diluents which can be used include starch, gelatin, glucose, lactose, fructose, maltose, magnesium carbonate, talc, magnesium stearate, methyl cellulose, carboxymethyl cellulose or its esters, gum arabic, polyethylene glycol, alkyl p-hydroxybenzoates, syrup, ethanol, propylene glycol, Vaseline, carbowax, glycerol, sodium chloride, sodium sulfite, sodium phosphate, citric acid, dichlorodifluoromethane, 1,2-dichlorotetrafluoroethane and sorbitan trioleate.

The medicaments may also contain other therapeutically effective drugs.

The dose of the compound of formula (I) can be varied widely depending upon the type of the animal to be treated, the route of administration, the severity of the patient's condition, the diagnosis of a physician, etc. Generally, it may be 0.1 to 5 mg/kg, preferably 0.3 to 3 mg/kg, per day. It is of course possible to administer the compound of formula (I) in dose larger than the above-specified upper limit or smaller than the above-specified lower limit according to the severity of the patient's condition and the physician's diagnosis. The above dose may be taken once a day or in several portions a day.

The following examples illustrate the present invention more specifically.

REFERENTIAL EXAMPLE 1

Production of 4-[4-(piperidinomethyl)pyridyl-2-oxy]-cis-2-butenamine

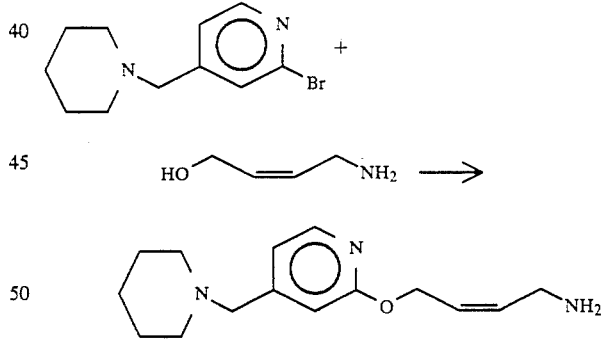

0.78 g of 60% sodium hydride was suspended in 20 ml of anhydrous tetrahydrofuran, and 1.54 g (17.7 mM) of 4-amino-cis-2-buten-1-ol was slowly added. The mixture was refluxed with stirring for 20 minutes. Then, under ice cooling, a solution of 3.00 g (11.8 mM) of 2-bromo-4-(piperidinomethyl)pyridine in 10 ml of tetrahydrofuran was added slowly to the mixture, and the entire mixture was then refluxed for 48 hours with stirring. After the reaction, the insoluble matter was removed by filtration, and the solvent was evaporated from the filtrate. The residue was extracted with 100 ml of dichloromethane three times. The extracts were dried over anhydrous magnesium sulfate, and the solvent was evaporated. The residue was purified by silica gel column chromatography using a 1:3 mixture of methanol and ethyl acetate as an eluent to give 1.49 g (yield 48%) of the compound as a pale brown oil.

¹H-NMR (δ, CDCl₃): 1.30–1.50 (2H, m), 1.50–1.65 (4H, m), 1.82 (2H, brs), 2.30–2.40 (4H, m), 3.40 (2H, s), 3.45 (2H, d, J=4.5 Hz), 4.88 (2H, d, J=4.5 Hz), 5.70–5.85 (2H, m), 6.72 (1H, s), 6.86 (1H, d, J=4.2 Hz), 8.05 (1H, d, J=4.2 Hz).

By the same procedure as described above, the following compounds were produced.

4-[4-(3-methylpiperidinomethyl)pyridyl-2-oxy]-cis-2-butenamine

¹H-NMR (δ, CDCl₃): 0.86 (3H, d, J=5.8 Hz), 1.50–1.84 (1H, m), 1.88–2.00 (2H, m), 2.60–2.80 (4H, m), 3.44 (2H, s), 3.46 (2H, d, J=4.0 Hz), 4.89 (2H, d, J=4.0 Hz), 5.68–5.83 (2H, m), 6.72 (1H, s), 6.86 (1H, d, J=4.2 Hz), 8.06 (1H, d, J=4.2 Hz).

4-[4-(1,2,3,6-tetrahydro-1-pyridylmethyl)pyridyl-2-oxy]-cis-2-butenamine

¹H-NMR (δ, CDCl₃): 2.18 (2H, dt, J=2.5 Hz, 5.6 Hz), 2.55 (2H, t, J=5.6 Hz), 2.97 (2H, dt, J=2.5 Hz, 2.6 Hz), 3.44 (2H, d, J=4.5 Hz), 3.52 (2H, s), 4.89 (2H, d, J=4.5 Hz), 5.60–5.82 (4H, m), 6.75 (1H, s), 6.91 (1H, d, J=5.4 Hz), 8.06 (1H, d, J=5.4 Hz).

4-[4-(1-perhydroazepinylmethyl)pyridyl-2-oxy]-cis-2-butenamine

¹H-NMR (δ, CDCl₃): 1.58–1.70 (8H, m), 2.45–2.70 (4H, m), 3.47 (2H, d, J=4.6 Hz), 3.58 (2H, s), 4.89 (2H, d, J=4.5 Hz), 5.68–5.80 (2H, m), 6.75 (1H, s), 6.89 (1H, d, J=5.4 Hz), 8.05 (1H, d, J=5.4 Hz).

4-[4-(4-methyl-1-piperazinylmethyl)pyridyl-2-oxy)-cis-2-butenamine

¹H-NMR (δ, CDCl₃): 1.50 (2H, brs), 2.30 (3H, s), 2.40–2.60 (8H, m), 3.45 (2H, s), 3.46 (2H, d, J=4.7 Hz), 4.88 (2H, d, J=4.7 Hz), 5.70–5.80 (2H, m), 6.73 (1H, s), 6.87 (1H, d, J=5.5 Hz), 8.06 (1H, d, J=5.5 Hz).

4-[4-(thiomorpholinomethyl)pyridyl-2-oxy]-cis-2-butenamine

¹H-NMR (δ, CDCl₃): 1.26 (2H, brs), 2.65–2.75 (8H, m), 3.45 (2H, s), 3.47 (2H, d, J=4.5 Hz), 4.89 (2H, d, J=4.5 Hz), 6.70–6.80 (2H, m), 6.72 (1H, s), 6.85 (1H, d, J=4.2 Hz), 8.05 (1H, d, J=4.2 Hz).

4-[4-(piperidinomethyl)pyridyl-2-oxy)-butanamine

¹H-NMR (δ, CDCl₃): 1.40–1.50 (4H, m), 1.50–1.70 (6H, m), 1.89 (2H, tt, J=6.6 Hz, 6.6 Hz), 2.30–2.45 (4H, m), 2.77 (2H, t, J=6.6 Hz), 3.40 (2H, s), 4.29 (2H, t, J=6.6 Hz), 6.70 (1H, s), 6.85 (1H, d, J=4.2 Hz), 8.05 (1H, d, J=4.2 Hz).

4-[4-(4-methyl-1-piperazinylmethyl)pyridyl-2-oxy]-butanamine

¹H-NMR (δ, CDCl₃): 1.25 (2H, brs), 1.61 (2H, tt, J=6.6 Hz, 6.6 Hz), 1.82 (2H, tt, J=6.6 Hz, 6.6 Hz), 2.91 (3H, s), 2.40–2.60 (8H, m), 2.77 (2H, t, J=6.6 Hz), 3.45 (2H, s), 4.29 (2H, t, J=6.6 Hz), 6.71 (1H, s), 6.85 (1H, d, J=4.2 Hz), 8.05 (1H, d, J=4.2 Hz).

EXAMPLE 1

Production of N-{4-[4-(piperidinomethyl)pyridyl-2oxy]-cis-2-butenyl)-2-(furfurylthio)acetamide

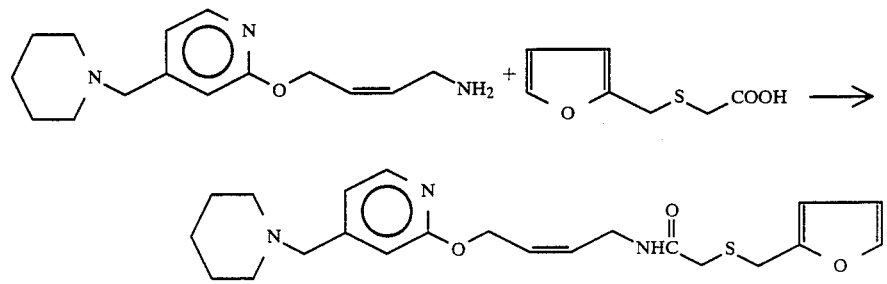

0.17 g (0.65 mM) of 4-[4-(piperidinomethyl)pyridyl-2-oxy]-cis-2-butenamine and 0.11 g (0.65 mM) of 2-(furfurylthio)acetic acid were dissolved in 20 ml of dichloromethane. To the resulting solution was added 0.15 g (0.78 mM) of 1-ethyl-3-(3-dimethylaminopropyl)carbodiimide hydrochloride, and the mixture was stirred for 18 hours. Then, 20 ml of dichloromethane and 20 ml of water were added to extract the reaction mixture. The dichloromethane layer was washed with 30 ml of water. The extract was dried over anhydrous magnesium sulfate, and the solvent was evaporated. The residue was purified by silica gel column chromatography using a 2:98 mixture of methanol and dichloromethane as an eluent to give 0.18 g (yield 67 %) of the captioned compound as an oil.

IR (cm⁻¹, film) 1655 (C=O)

¹H-NMR (δ, CDCl₃): 1.40–1.50 (2H, m), 1.50–1.65, (4H, m), 2.30–2.45 (4H, m), 3.23 (2H, s), 3.41 (2H, s), 3.74 (2H, s), 3.99 (2H, dd, J=6.1 Hz, 6.1 Hz), 4.91 (2H, d, J=6.1 Hz), 5.55–5.70 (1H, m), 5.80–5.95 (1H, m), 6.20 (1H, d, J=3.2 Hz), 6.30 (1H, dd, J=3.2, 1.4 Hz), 6.74 (1H, s), 6.80–6.95 (1H, brs), 6.88 (1H, d, J=4.3 Hz), 7.36 (1H, d, J=1.4 Hz), 8.06 (1H, d, J=4.3 Hz).

Mass: as C₂₂H₂₉N₃O₃S: Calculated: 415, 1930. Found: 415, 1931.

EXAMPLE 2

Production of N-{4-[4-(piperidinomethyl)pyridyl-2-oxy]-cis-2-butenyl}-2-(furfurylsulfinyl)acetamide

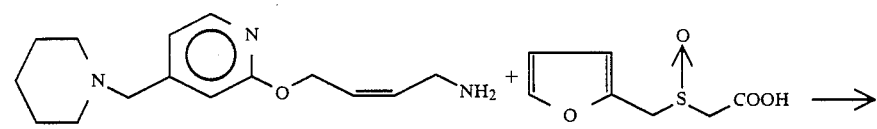

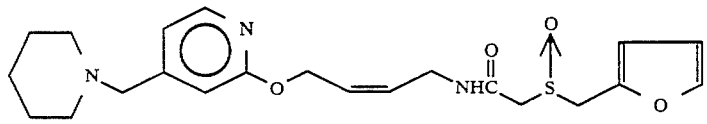

The captioned compound was produced (yield 37%) by repeating the reaction of Example 1 except that 0.12 g (0.65 mM) of 2-(furfurylsulfinyl)acetic acid was used instead of the 2-(furfurylthio)acetic acid. Recrystallization from a mixture of benzene and hexane gave colorless crystals.

Melting point: 92.7°–94.9° C.

IR (cm$^{-1}$, KBr Tab.): 1645 (C=O), 1041 (S→O).

$^1$H-NMR (δ, CDCl$_3$): 1.40–1.50 (2H, m), 1.50–1.65 (4H, m), 2.30–2.45 (4H, m), 3.34 (1H, d, J=14.2 Hz), 3.40 (2H, s), 3.69 (1H, d, J=14.2 Hz), 4.15 (2H, dd, J=6.1 Hz, 6.1 Hz), 4.14 (1H, d, J=14.2 Hz), 4.38 (1H, d, J=14.2 Hz), 4.93 (2H, t, J=6.1 Hz), 5.60–5.75 (1H, m), 5.80–5.90 (1H, m), 6.40 (1H, dd, J=3.1 Hz, 1.6 Hz), 6.47 (1H, d, J=3.1 Hz), 6.73 (1H, s), 6.87 (1H, d, J=5.1 Hz), 7.15–7.25 (1H, brs), 7.44 (1H, d, J=1.6 Hz), 8.04 (1H, d, J=5.1 Hz).

Mass: as C$_{22}$H$_{29}$N$_3$O$_4$S: Calculated: 431.1879. Found: 431.1883.

EXAMPLE 3

Production of N-{4-[4-(piperidinomethyl)pyridyl-2-oxy]-cis-2-butenyl}-2-(3-furylmethylsulfonyl)acetamide

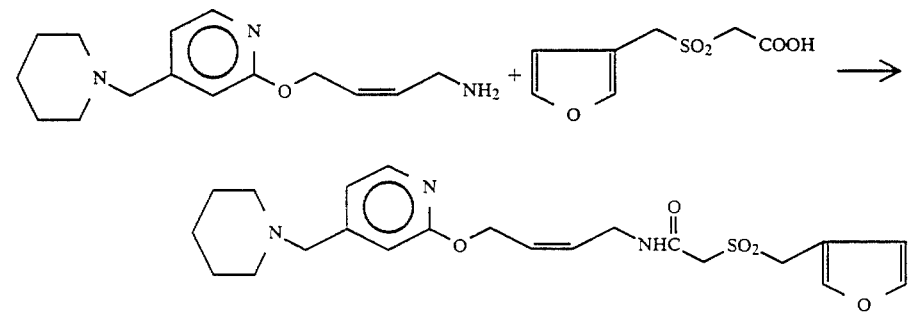

The captioned compound was obtained as a colorless oil (yield 51%) by repeating Example 1 except that 0.13 g (0.65 mM) of 2-(3-furylmethylsulfonyl)acetic acid was used instead of the 2-(furfurylthio)acetic acid.

IR (cm$^{-1}$, film) 1680 (C=O), 1319, 1118 (SO$_2$).

$^1$H-NMR (δ, CDCl$_3$): 1.40–1.50 (2H, m), 1.50–1.70 (4H, m), 2.30–2.45 (4H, m), 3.42 (2H, s), 3.75 (2H, s), 4.09 (2H, t, J=5.9 Hz), 4.34 (2H, s), 4.94 (2H, d, J=5.9 Hz), 5.6–5.75 (1H, m), 5.80–5.90 (1H, m), 6.60 (1H, d, J=1.8 Hz), 6.75 (1H, s), 6.91 (1H, d, J=5.1 Hz), 7.25–7.4 (1H, brs), 7.45 (1H, d, J=1.8 Hz), 7.65 (1H, s), 8.05 (1H, d, J=5.1 Hz).

Mass: as C$_{22}$H$_{29}$N$_3$O$_5$S: Calculated: 447.1829. Found: 447.1820.

EXAMPLE 4

Production of N-{4-[4-(dimethylaminomethyl)pyridyl-2-oxy]-cis-2-butenyl}-2-(furfurylsulfinyl)acetamide

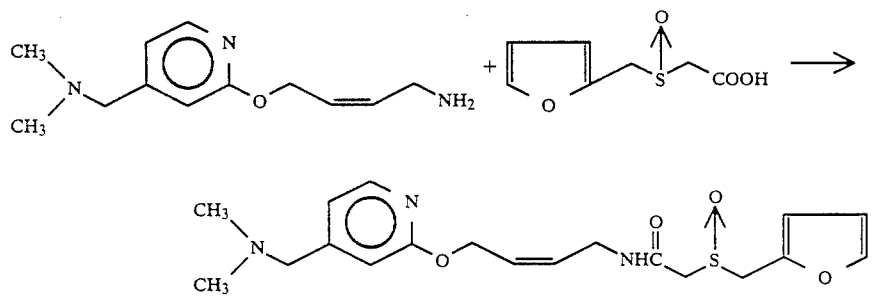

The captioned compound was obtained (yield 38%) by repeating Example 2 except that 0.65 mM of 4-[4-(dimethylaminomethyl)pyridyl-2-oxy]-cis-2-butenamine was used instead of the 4-[4-(piperidinomethyl)pyridyl-2-oxy]-cis-2-butenamine.

IR (cm$^{-1}$, film) 1666 (C=O), 1040 (S→O).

$^1$H-NMR (δ, CDCl$_3$): 2.24 (6H, s), 3.33 (1H, d, J=14.2 Hz), 3.37 (2H, s), 3.59 (1H, d, J=14.2 Hz), 4.11 (2H, dd, J=6.8 Hz, 6.0 Hz), 4.19 (1H, d, J=13.3 Hz), 4.26 (1H, d, J=13.3 Hz), 4.93 (2H, d, J=6.4 Hz), 5.62–5.74 (1H, m), 5.80–5.90 (1H, m), 6.39 (1H, dd, J=2.9 Hz, 2.1 Hz), 6.47 (1H, d, J=2.9 Hz), 6.71 (1H, s), 6.87 (1H, d, J=5.6 Hz), 7.11 (1H, brs), 7.44 (1H, d, J=2.1 Hz), 8.07 (1H, d, J=5.6 Hz).

Mass: as C$_{19}$H$_{25}$N$_3$O$_4$S: Calculated: 391.1566. Found: 391.1563.

EXAMPLE 5

Production of N-{4-[4-(dimethylaminomethyl)pyridyl-2-oxy]-cis-2-butenyl}-2-(3-furylmethylsulfonyl)acetamide

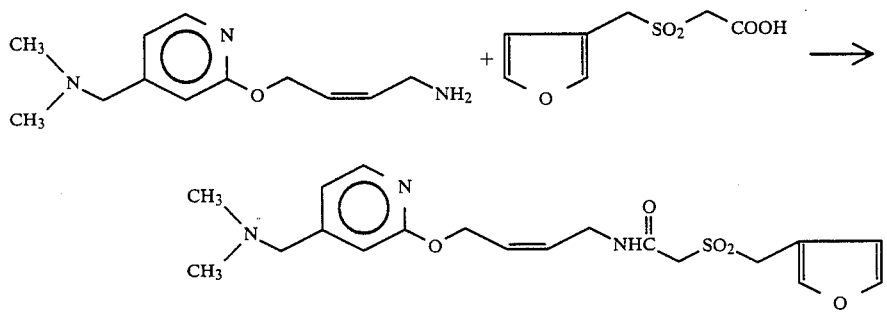

The captioned compound was obtained (yield 66%) by repeating Example 3 except that 0.65 mM of 4-[4-(dimethylaminomethyl)pyridyl-2-oxy]-cis-2-butenamine was used instead of the 4-[4-(piperidinomethyl)-pyridyl-2-oxy]-cis-2-butenamine.

IR (cm$^{-1}$, film) 1680 (C=O), 1322, 1118 (SO$_2$).

$^1$H-NMR (δ, CDCl$_3$): 2.24 (6H, s), 3.37 (2H, s), 3.75 (2H, s), 4.09 (2H, dd, J=6.3, 5.6 Hz), 4.34 (2H, s), 4.94 (2H, d, J=5.6 Hz), 5.63–5.73 (1H, m), 5.80–5.90 (1H, m), 6.59 (1H, d, J=1.5 Hz), 6.72 (1H, s), 6.89 (1H, d, J=5.6 Hz), 7.24 (1H, brs), 7.46 (1H, dd, J=1.5 Hz, 1.0 Hz), 7.65 (1H, d, J=1.0 Hz), 8.07 (1H, d, J=5.6 Hz).

Mass: as C$_{19}$H$_{25}$N$_3$O$_5$S: Calculated: 407.1515. Found: 407.1510.

EXAMPLE 6

Production of N-{4-[4-(dimethylaminomethyl)pyridyl-2-oxy]-cis-2-butenyl}-2-(3-furylmethylthio)acetamide

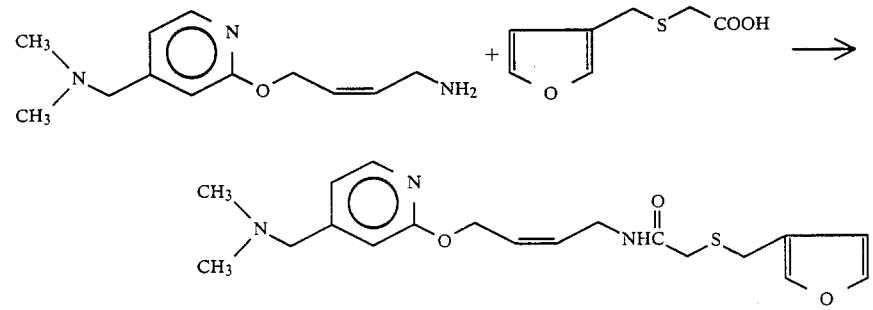

The captioned compound was obtained (yield 20%) by repeating Example 5 except that 0.65 mM of 2-(3-furylmethylthio)acetic acid was used instead of the 2-(3-furylmethylsulfonyl)acetic acid.

IR (cm$^{-1}$, film): 1652 (C=O), $^1$H-NMR (δ, CDCl$_3$): 2.26 (6H, s), 3.16 (2H, s), 3.39 (2H, s), 3.57 (2H, s), 4.03 (2H, dd, J=6.1 Hz, 6.1 Hz), 4.93 (2H, d, J=6.1 Hz), 5.58–5.70 (1H, m), 5.81–5.92 (1H, m), 6.36 (1H, d, J=1.5 Hz), 6.73 (1H, s), 6.88 (1H, brs), 6.89 (1H, d, J=5.1 Hz), 7.35 (1H, s), 7.38 (1H, d, J=1.5 Hz), 8.08 (1H, d, J=5.1 Hz).

EXAMPLE 7

Production of N-{4-[4-(dimethylaminomethyl)pyridyl-2-oxy]-cis-2-butenyl}-2-(furfurylsulfonyl)acetamide

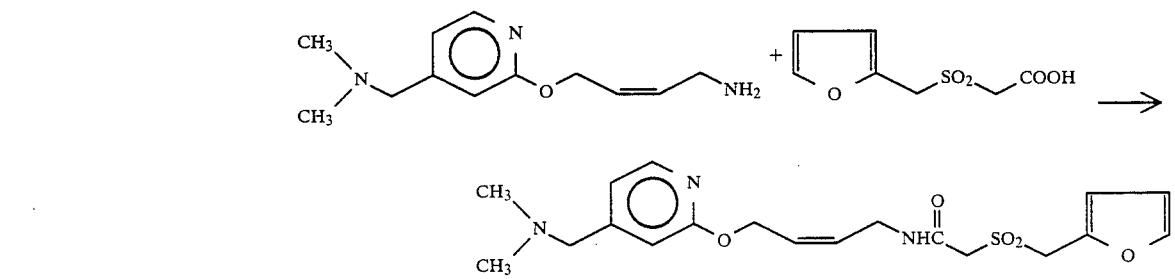

The captioned compound was obtained (yield 25%) by repeating Example 5 except that 0.65 mM of 2-(furfurylsulfonyl)acetic acid was used instead of the 2-(3-furylmethylsulfonyl)acetic acid.

IR (cm$^{-1}$, film): 1668 (C=O), 1320, 1150 (SO$_2$).

$^1$H-NMR (δ, CDCl$_3$): 2.26 (6H, s), 3.39 (2H, s), 3.85 (2H, s), 4.09 (2H, dd, J=6.3 Hz, 6.3 Hz), 4.58 (2H, s), 4.94 (2H, d, J=6.3 Hz), 5.62–5.72 (1H, m), 5.80–5.90 (1H, m), 6.43 (1H, dd, J=3.1 Hz, 2.1 Hz), 6.62 (1H, d, J=3.1 Hz), 6.74 (1H, s), 6.89 (1H, d, J=5.0 Hz), 7.24

(1H, brs), 7.49 (1H, d, J=2.1 Hz), 8.07 (1H, d, J=5.0 Hz).

EXAMPLE 8

Production of
N-{4-[4-(3-methylpiperidinomethyl)pyridyl-2-oxy]-cis-2-butenyl}-2-(furfurylsulfinyl)acetamide

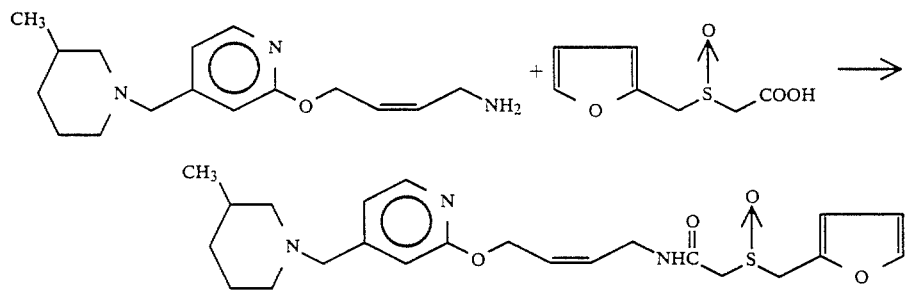

The captioned compound was obtained (yield 43%) by repeating Example 2 except that 0.65 mM of 4-[4-(3-methylpiperidinomethyl)pyridyl-2-oxy]-cis-2-butenamine was used instead of the 4-[4-(piperidinomethyl)-pyridyl-2-oxy]-cis-2-butenamine.

IR (cm$^{-1}$, film) 1666 (C=O), 1036 (S→O).

$^1$H-NMR (δ, CDCl$_3$): 0.84 (3H, d, J=5.6 Hz), 1.54–1.73(6H, m), 1.84–1.94 (1H, m), 2.69–2.78 (2H, m), 3.33 (1H, d, J=14.1 Hz), 3.40 (2H, s), 3.59 (1H, d, J=14.1 Hz), 4.11 (1H, dd, J=5.0 Hz, 7.0 Hz), 4.19 (1H, d, J=13.4 Hz), 4.26 (1H, d, J=13.4 Hz), 4.93 (2H, d, J=7.1 Hz), 5.66–5.72 (1H, m), 5.82–5.90 (1H, m), 6.39 (1H, dd, J=3.4 Hz, 2.0 Hz), 6.47 (1H, d, J=3.4 Hz), 6.73 (1H, s), 6.87 (1H, d, J=5.4 Hz), 7.15 (1H, brs), 7.44 (1H, d, J=2.0 Hz), 8.05 (1H, d, J=5.4 Hz).

Mass: as C$_{23}$H$_{31}$N$_3$O$_4$S: Calculated: 445.2034. Found: 445.2029.

EXAMPLE 9

Production of
N-{4-[4-(3-methylpiperidinomethyl)pyridyl-2-oxy]-cis-2-butenyl}-2-(3-furylmethylsulfonyl)acetamide

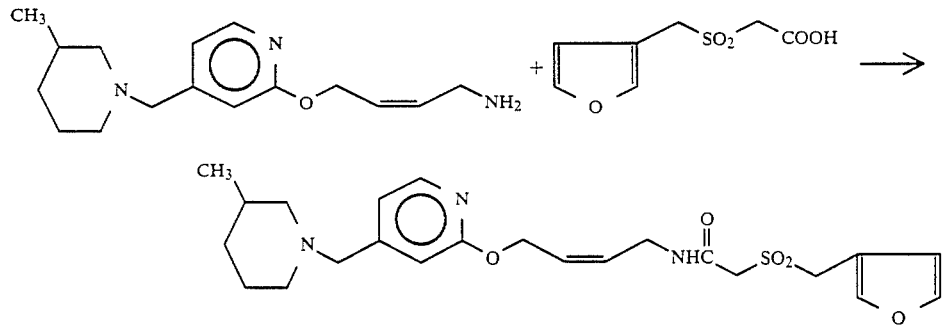

The captioned compound was obtained (yield 50%) by repeating Example 3 except that 0.65 mM of 4-[4-(3-methylpiperidinomethyl)pyridyl-2-oxy]-cis-2-butenamine was used instead of the 4-[4-(piperidinomethyl)-pyridyl-2-oxy]-cis-2-butenamine.

IR (cm$^{-1}$, film): 1678 (C=O), 1318, 1118 (SO$_2$).

1H-NMR (δ, CDCl$_3$): 0.84 (3H, d, J=6.1 Hz), 1.55–1.85 (6H, m), 1.85–1.95 (1H, m), 2.66–2.78 (2H, m), 3.41 (2H, s), 3.75 (2H, s), 4.09 (2H, dd, J=5.9 Hz, 6.1 Hz), 4.34 (2H, s), 4.94 (2H, d, J=6.3 Hz), 5.64–5.72 (1H, m), 5.82–5.90 (1H, m), 6.60 (1H, s), 6.74 (1H, s), 6.89 (1H, d, J=5.4 Hz), 7.33 (1H, brs), 7.46 (1H, s), 7.66 (1H, s), 8.05 (1H, d, J=5.4 Hz).

Mass: as C$_{23}$H$_{31}$N$_3$O$_5$S: Calculated: 461.1984. Found: 461.1998.

EXAMPLE 10

Production of
N-{4-[4-(pyrrolidinomethyl)pyridyl-2-oxy]-cis-2-butenyl}-2-(furfurylsulfinyl)acetamide

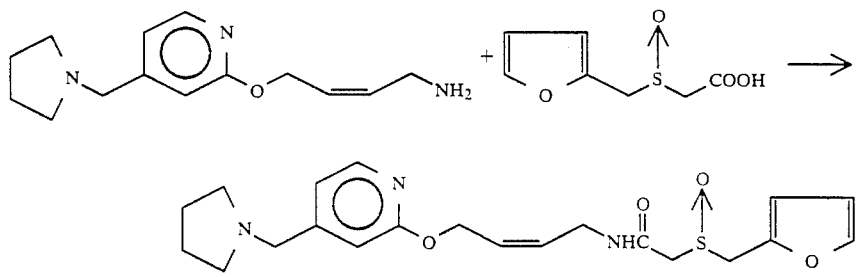

The captioned compound was obtained (yield 41%) by repeating Example 2 except that 0.65 mM of 4-[4-

(pyrrolidinomethyl)pyridyl-2-oxy]-cis-2-butenamine was used instead of the 4-[4-(piperidinomethyl)pyridyl-2-oxy]-cis-2-butenamine.

IR (cm$^{-1}$, film): 1672 (C=O), 1040 (S→O).

$^1$H-NMR (δ, CDCl$_3$): 1.75–1.84 (4H, m), 2.48–2.55 (4H, m), 3.35 (2H, d, J=14.9 Hz), 4.10 (1H, dd, J=5.9 Hz, 6.3 Hz), 4.19 (2H, d, J=14.2 Hz), 4.27 (2H, d, J=14.2 Hz), 4.93 (1H, d, J=6.6 Hz), 5.62–5.72 (1H, m), 5.80–5.90 (1H, m), 6.39 (1H, dd, J=2.9 Hz, 1.8 Hz), 6.47 (1H, d, J=2.9 Hz), 6.88 (1H, d, J=5.1 Hz), 7.28 (1H, s), 7.43 (1H, d, J=1.8 Hz), 8.05 (1H, d, J=5.1 Hz).

Mass: as C$_{21}$H$_{27}$N$_3$O$_4$S: Calculated: 417.1722. Found: 417.1716.

EXAMPLE 11

Production of N-{4-[4-(pyrrolidinomethyl)pyridyl-2-oxy]-cis-2-butenyl}-2-(3-furylmethylsulfonyl)acetamide

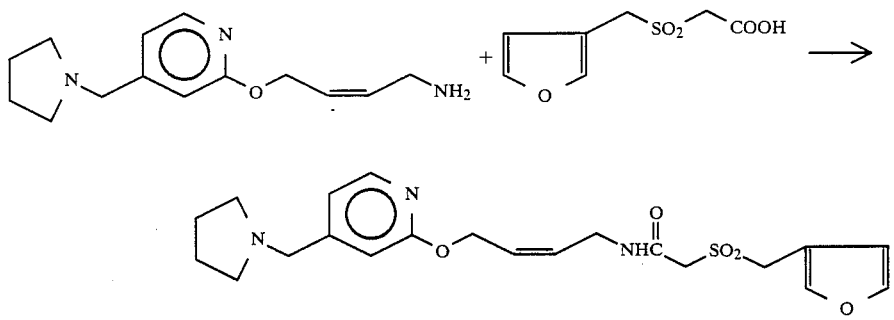

The captioned compound was obtained (yield 49%) by repeating Example 3 except that 0.65 mM of 4-[4-(pyrrolidinomethyl)pyridyl-2-oxy]-cis-2-butenamine was used instead of the 4-[4-(piperidinomethyl)pyridyl-2-oxy]-cis-2-butenamine.

IR (cm$^{-1}$, film): 1680 (C=O), 1324, 1118 (SO$_2$).

$^1$H-NMR (δ, CDCl$_3$): 1.65–1.85 (4H, m), 2.47–2.54 (4H, m), 3.57 (2H, s), 3.75 (2H, s), 4.09 (2H, dd, J=5.8 Hz, 6.4 Hz), 4.34 (2H, s), 4.94 (2H, d, J=7.8 Hz), 6.60 (1H, d, J=1.8 Hz), 6.65–6.75 (1H, m), 6.75 (1H, s), 6.80–6.92 (1H, m), 6.90 (1H, d, J=4.4 Hz), 7.25–7.32 (1H, m), 7.46 (1H, d, J=1.8 Hz), 7.66 (1H, s), 8.05 (1H, d, J=4.4 Hz).

Mass as C$_{21}$H$_{27}$N$_3$O$_5$S: Calculated: 433.1670. Found: 433.1662.

EXAMPLE 12

Production of N-{4-[4-(morpholinomethyl)pyridyl-2-oxy]-cis-2-butenyl}-2-(furfurylsulfinyl)acetamide

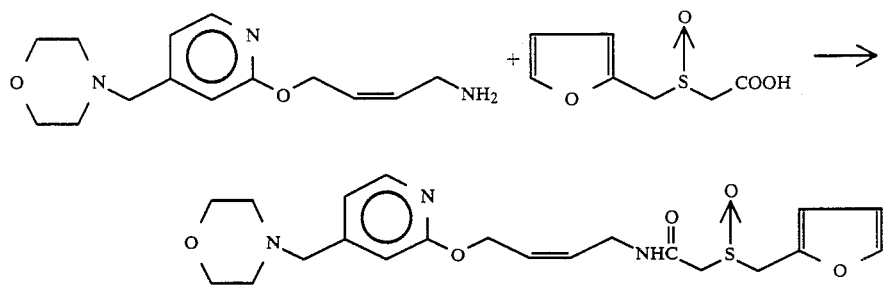

The captioned compound was obtained (yield 35%) by repeating Example 2 except that 0.65 mM of 4-[4-(morpholinomethyl)pyridyl-2-oxy]-cis-2-butenamine was used instead of the 4-[4-(piperidinomethyl)pyridyl-2-oxy]-cis-2-butenamine.

IR (cm$^{-1}$, film): 1666 (C=O), 1036 (S→O).

$^1$H-NMR (δ, CDCl$_3$): 2.44 (4H, t, J=4.4 Hz), 3.32 (1H, d, J=14.5 Hz), 3.44 (2H, s), 3.59 (1H, d, J=14.5 Hz), 3.72 (4H, t, J=4.4 Hz), 4.11 (2H, dd, J=6.4 Hz, 6.1 Hz), 4.18 (1H, d, J=14.1 Hz), 4.26 (1H, d, J=14.1 Hz), 4.93 (2H, d, J=7.0 Hz), 5.62–5.72 (1H, m), 5.80–5.90 (1H, m), 6.39 (1H, dd, J=3.5 Hz, 1.7 Hz), 6.47 (1H, d, J=3.5 Hz), 6.74 (1H, s), 6.88 (1H, d, J=5.1 Hz), 7.05–7.15 (1H, m), 7.44 (1H, d, J=1.7 Hz), 8.06 (1H, d, J=5.1 Hz).

Mass: as C$_{21}$H$_{27}$N$_3$O$_5$S: Calculated: 433.1671. Found: 433.1671.

EXAMPLE 13

Production of N-{4-[4-(1,2,3,6-tetrahydro-1-pyridylmethyl)pyridyl-2-oxy]-cis-2-butenyl}-2-(furfurylsulfinyl)acetamide

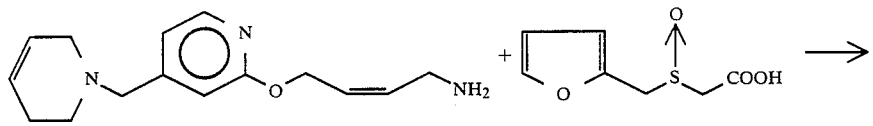

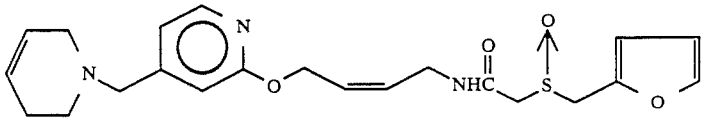

The captioned compound was obtained (yield 36%) by repeating Example 2 except that 0.65 mM of 4-[4-(1,2,3,6-tetrahydro-1-pyridylmethyl)pyridyl-2-oxy]-cis-2-butenamine was used instead of the 4-[4-(piperidinomethyl)pyridyl-2-oxy]-cis-2-butenamine.

IR (cm$^{-1}$, film) 1668 (C=O), 1040 (S→O).

$^1$H-NMR (δ, CDCl$_3$): 2.18 (2H, dt, J=2.5 Hz, 5.6 Hz), 2.55 (2H, t, J=5.6 Hz), 2.97 (2H, dt, J=2.5 Hz, 2.6 Hz), 3.33 (1H, d, J=14.0 Hz), 3.52 (2H, s), 3.59 (1H, d, J=14.0 Hz), 4.11 (2H, dd, J=5.9 Hz, 6.6 Hz), 4.18 (1H, d, J=13.9 Hz), 4.26 (1H, d, J=13.9 Hz), 4.93 (2H, d, J=6.6 Hz), 5.60–5.90 (4H, m), 6.39 (1H, dd, J=3.1 Hz, 1.2 Hz), 6.47(1H, d, J=3.1 Hz), 6.91 (1H, d, J=5.4 Hz), 7.15 (1H, brs), 7.44 (1H, d, J=1.2 Hz), 8.06 (1H, d, J=5.4 Hz).

Mass: as C$_{22}$H$_{27}$N$_3$O$_4$S: Calculated: 429.1722. Found: 429.1708.

EXAMPLE 14

Production of N-{4-[4-(1,2,3,6-tetrahydro-1-pyridylmethyl)pyridyl-2-oxy]-cis-2-butenyl}-2-(3-furylmethylsulfonyl)acetamide

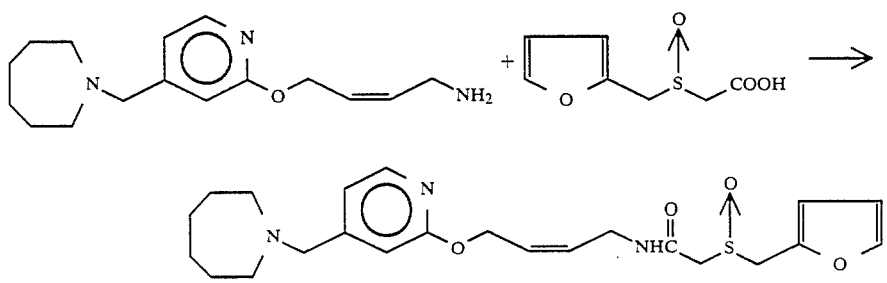

The captioned compound was obtained (yield 52%) by repeating Example 3 except that 0.65 mM of 4-[4-(1,2,3,6-tetrahydro-1-pyridylmethyl)pyridyl-2-oxy]-cis-2-butenamine was used instead of the 4-[4-(piperidinomethyl)pyridyl-2-oxy]-cis-2-butenamine.

IR (cm$^{-1}$, film): 1678 (C=O), 1318, 1118 (SO$_2$).

$^1$H-NMR (δ, CDCl$_3$): 2.18 (2H, dt, J=5.5 Hz, 3.0 Hz), 2.55 (2H, t, J=5.5 Hz), 2.97 (2H, dt, J=3.0 Hz, 2.2 Hz), 3.52 (2H, s), 3.75 (2H, s), 4.08 (2H, dd, J=5.9 Hz, 6.3 Hz), 4.34 (2H, s), 4.93 (2H, d, J=6.5 Hz), 5.61–5.90 (4H, m), 6.59 (1H, d, J=1.0 Hz), 6.77 (1H, s), 6.93 (1H, d, J=5.4 Hz), 7.26 (1H, brs), 7.46 (1H, dd, J=1.0 Hz, 1.0 Hz), 7.65 (1H, d, J=1.0 Hz), 8.06 (1H, d, J=5.4 Hz).

Mass: as C$_{22}$H$_{27}$N$_3$O$_5$S:
Calculated: 445.1671.
Found: 445.1663.

EXAMPLE 15

Production of N-{(4-[4-(1-perhydroazepinylmethyl)pyridyl-2-oxy]-cis-2-butenyl}-2-(furfurylsulfinyl)-acetamide

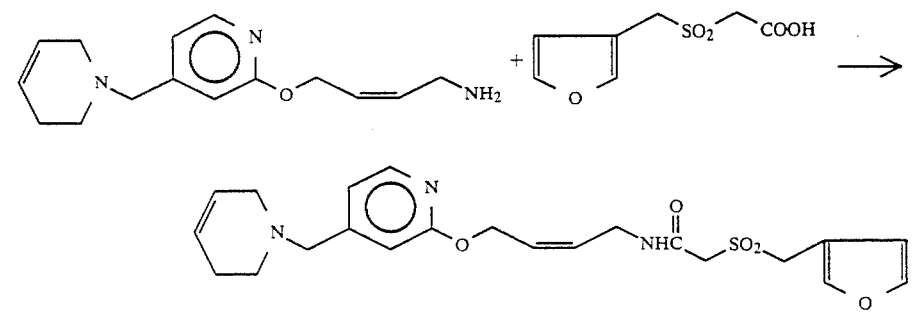

The captioned compound was obtained (yield 34%) by repeating Example 2 except that 0.65 mM of 4-[4-(1-perhydroazepinylmethyl)pyridyl-2-oxy]-cis-2-butenamine was used instead of the 4-[4-(piperidinomethyl)-pyridyl-2-oxy]-cis-2-butenamine.

IR (cm$^{-1}$, film): 1668 (C=O), 1034 (S→O).

$^1$H-NMR (δ, CDCl$_3$): 1.55–1.78 (8H, m), 2.55–2.62 (4H, m), 3.33 (1H, d, J=15.1 Hz), 3.58 (2H, s), 3.59 (1H, d, J=15.1 Hz), 4.11 (2H, dd, J=6.4 Hz, 5.8 Hz), 4.18 (1H, d, J=14.4 Hz), 4.26 (1H, d, J=14.4 Hz), 4.93 (2H, d, J=6.4 Hz), 5.64–5.73 (1H, m), 5.80–5.91 (1H, m), 6.39 (1H, dd, J=2.8 Hz, 1.4 Hz), 6.47 (1H, d, J=2.8 Hz), 6.75 (1H, s), 6.90 (1H, d, J=5.5 Hz), 7.16 (1H, brs), 7.44 (1H, d, J=1.4 Hz), 8.04 (1H, d, J=5.5 Hz).

Mass: as C$_{23}$H$_{31}$N$_3$O$_4$S:
Calculated: 445.2034. Found: 445.2018.

EXAMPLE 16

Production of
N-{4-[4-(1-perhydroazepinylmethyl)pyridyl-2-oxy]-cis-2-butenyl}-2-(3-furylmethylsulfonyl)acetamide

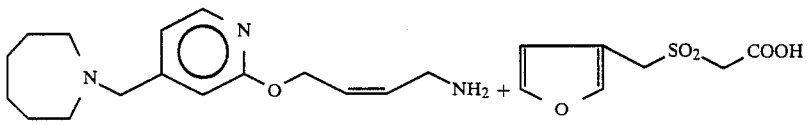

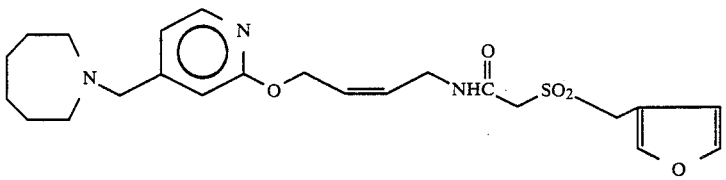

The captioned compound was obtained (yield 41%) by repeating Example 3 except that 0.65 mM of 4-[4-(1-perhydroazepinylmethyl)pyridyl-2-oxy]-cis-2-butenamine was used instead of the 4-[4-(piperidinomethyl)-pyridyl-2-oxy]-cis-2-butenamine.

IR (cm$^{-1}$, film): 1680 (C=O), 1320, 1118 (SO$_2$).

$^1$H-NMR (δ, CDCl$_3$): 1.55–1.78 (8H, m), 2.55–2.65 (4H, m), 3.58 (2H, s), 3.77 (2H, s), 4.08 (2H, dd, J=5.9 Hz, 5.8 Hz), 4.35 (2H, s), 4.93 (2H, d, J=5.9 Hz), 5.63–5.73 (1H, m), 5.80–5.90 (1H, m), 6.59 (1H, d, J=1.0 Hz), 6.76 (1H, s), 6.91 (1H, d, J=5.4 Hz), 7.39 (1H, brs), 7.45 (1H, dd, J=1.0 Hz, 1.0 Hz), 7.65 (1H, d, J=1.0 Hz), 8.04 (1H, d, J=5.4 Hz).

Mass: as C$_{23}$H$_{31}$N$_3$O$_5$S:
Calculated: 461.1984.
Found: 461.1984.

The captioned compound was obtained (yield 37%) by repeating Example 2 except that 0.65 mM of 4-[4-(4-methyl-1-piperazinylmethyl)pyridyl-2-oxy]-cis-2-butenamine was used instead of the 4-[4-(piperidinomethyl)-pyridyl-2-oxy]-cis-2-butneamine.

IR (cm$^{-1}$, film): 1665 (C=O), 1040 (S→O).

$^1$H-NMR (δ, CDCl$_3$): 2.29 (3H, s), 2.40–2.60 (8H, m), 3.32 (1H, d, J=13.4 Hz), 3.45 (2H, s), 3.60 (1H, d, J=13.4 Hz), 4.11 (2H, dd, J=6.3 Hz, 6.3 Hz), 4.18 (1H, d, J=14.2 Hz), 4.27 (1H, d, J=14.2 Hz), 4.93 (2H, d, J=6.6 Hz), 5.62–5.73 (1H, m), 5.80–5.90 (1H, m), 6.40 (1H, dd, J=3.5 Hz, 2.0 Hz), 6.47 (1H, d, J=3.5 Hz), 6.74 (1H, s), 6.87 (1H, d, J=5.0 Hz), 7.13 (1H, brs), 7.44 (1H, d, J=2.0 Hz), 8.05 (1H, d, J=5.0 Hz).

Mass: as C$_{22}$H$_{30}$N$_4$O$_4$S:
Calculated: 446.1987.
Found: 446.1978.

EXAMPLE 18

Production of
N-{4-[4-(4-methyl-1-piperidinylmethyl)pyridyl-2-oxy]-cis-2-butenyl}-2-(3-furylmethylsulfonyl)acetamide

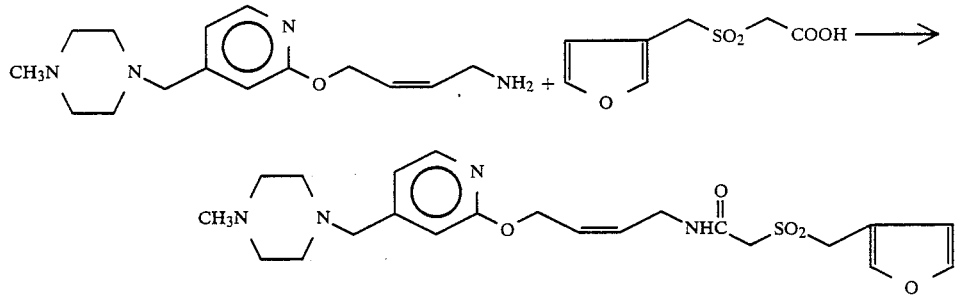

EXAMPLE 17

Production of
N-{4-[4-(4-methyl-1-piperazinylmethyl)pyridyl-2-oxy]-cis-2-butenyl}-2-(furfurylsulfinyl)-acetamide The captioned compound was obtained (yield 55%) by repeating Example 3 except that 0.65 mM of 4-[4-(4-

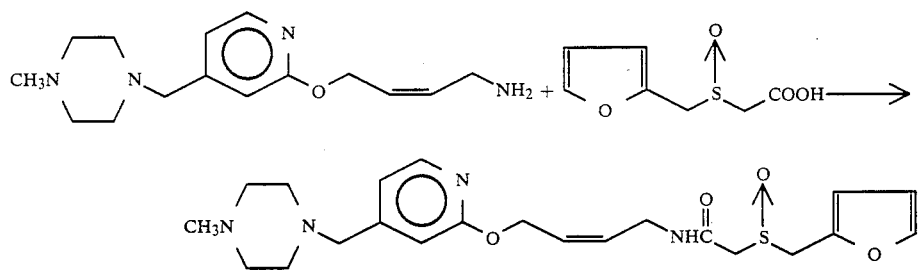

methyl-1-piperidinylmethyl)pyridyl-2-oxy]-cis-2-butenamine was used instead of the 4-[4-(piperidinomethyl)-pyridyl-2-oxy]-cis-2-butenamine.

IR (cm$^{-1}$, film): 1680 (C=O) 1310, 1120 (SO$_2$).

$^1$H-NMR (δ, CDCl$_3$): 2.30 (3H, s), 2.45–2.60 (8H, m), 3.46 (2H, s), 3.76 (2H, s), 4.69 (2H, dd, J=5.4 Hz, 5.6 Hz), 4.34 (2H, s), 4.93 (2H, d, J=7.0 Hz), 5.62–5.73 (1H, m), 5.80–5.92 (1H, m), 6.59 (1H, d, J=1.4 Hz), 6.75 (1H, s), 6.89 (1H, d, J=5.4 Hz), 7.28 (1H, brs), 7.46 (1H, d, J=1.4 Hz), 7.65 (1H, s), 8.05 (1H, d, J=5.4 Hz).

4.28 (1H, d, J=13.9 Hz), 4.93 (2H, d, J=6.6 Hz), 5.64–5.74 (1H, m), 5.80–5.90 (1H, m), 6.40 (1H, dd, J=3.5 Hz, 6.1 Hz), 6.47 (1H, d, J=3.5 Hz), 6.72 (1H, s), 6.85 (1H, d, J=5.1 Hz), 7.20 (1H, brs), 7.44 (1H, d, J=1.6 Hz), 8.06 (1H, d, J=5.1 Hz).

EXAMPLE 20

Production of N-{4-[4-(thiomorpholinomethyl)-pyridyl-2-oxy]-cis-2-butenyl}-2-(3-furylmethylsulfonyl)-acetamide

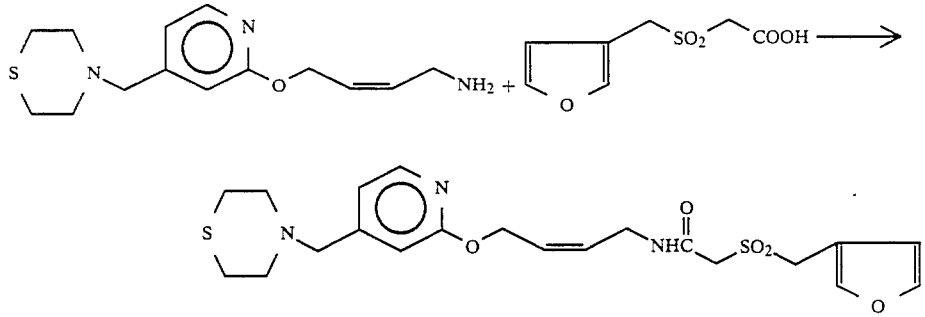

Mass: as C$_{22}$H$_{30}$N$_4$O$_5$S:
Calculated: 462.1937.
Found: 462.1939.

EXAMPLE 19

Production of N-{4-[4-(thiomorpholinomethyl)-pyridyl-2-oxy]-cis-2-butenyl}-2-(furfurylsulfinyl)-acetamide The captioned compound was obtained (yield 24%) by repeating Example 3 except that 0.65 mM of 4-[4-(thiomorpholinomethyl)pyridyl-2-oxy]-cis-2-butenamine was used instead of the 4-[4-(piperidinomethyl)-pyridyl-2-oxy]-cis-2-butenamine.

IR (cm$^{-1}$, film): 1678 (C=O),
1318, 1118 (SO$_2$).

$^1$H-NMR (δ, CDCl$_3$): 2.60–2.80 (8H, m), 3.46 (2H, s),

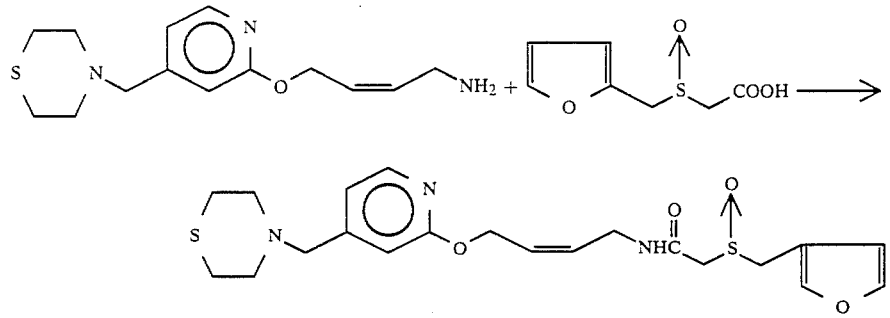

The captioned compound was obtained (yield 12%) by repeating Example 2 except that 0.65 mM of 4-[4-(thiomorpholinomethyl)pyridyl-2-oxy]-cis-2-butenamine was used instead of the 4-[4-(piperinomethyl)pyridyl-2-oxy]-cis-2-butenamine.

IR (cm$^{-1}$, film): 1666 (C=O),
1036 (S→O).

$^1$H-NMR (δ, CDCl$_3$): 2.60–2.80 (8H, m), 3.34 (1H, d, 14.1 Hz), 3.45 (2H, s), 3.59 (1H, d, J=14.1 Hz), 4.10 (2H, dd, J=6.4 Hz, 5.0 Hz), 4.18 (1H, d, J=13.9 Hz), 3.77 (2H, s), 4.08 (2H, dd, J=5.8 Hz, 6.2 Hz), 4.34 (2H, s), 4.94 (2H, d, J=6.6 Hz), 5.64–5.74 (1H, m), 5.80–5.92 (1H, m), 6.59 (1H, s), 6.74 (1H, s), 6.87 (1H, d, J=5.2 Hz), 7.29 (1H, brs), 7.46 (1H, s), 7.65 (1H, s), 8.06 (1H, d, J=5.2 Hz).

EXAMPLE 21

Production of N-{4-[4-(piperidinomethyl)-pyridyl-2-oxy]-butyl}-2-(furfurylsulfinyl)acetamide

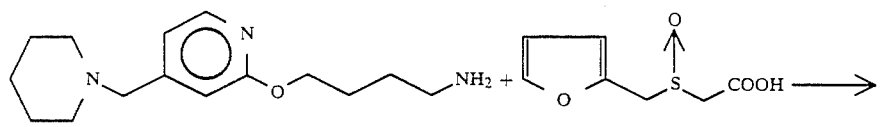

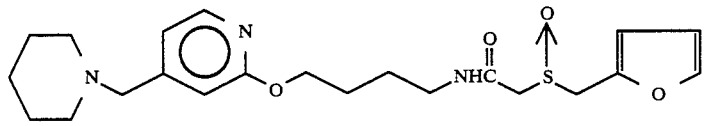

The captioned compound was obtained by repeating Example 2 except that 0.65 mM of 4-[4-(piperidinomethyl)pyridyl-2-oxy]butanamine was instead of the 4-[4-(piperidinomethyl)pyridyl-2-oxy]-cis-2-butenamine. Recrystallization from hexane gave a colorless powder in a yield of 24%.

Melting point: 102.8°–104.3° C.

IR (cm$^{-1}$, KBr Tab.): 1647 (C=O), 1050 (S→O).

$^1$H-NMR (δ, CDCl$_3$): 1.40–1.65 (6H, m), 1.65–1.90 (4H, m), 2.30–2.45 (4H, m), 3.31 (1H, d, J=14.5 Hz), 3.40 (2H, s), 3.41 (2H, dt, J=6.1 Hz, 6.1 Hz), 3.58 (1H, d, J=14.5 Hz), 4.16 (1H, d, J=13.9 Hz), 4.26 (1H, d, J=13.9 Hz), 4.30 (2H, t, J=6.1 Hz), 6.40 (1H, dd, J=3.5 Hz, 2.0 Hz), 6.47 (1H, d, J=3.5 Hz), 6.90 (1H, s), 6.85 (1H, dd, J=5.4 Hz, 1.3 Hz), 6.95 (1H, brs), 7.44 (1H, d, J=2.0 Hz), 8.03 (1H, d, J=5.4 Hz).

Mass: as C$_{22}$H$_{31}$N$_3$O$_4$S:
Calculated: 433.2036.
Found: 433.2037.

EXAMPLE 22

Production of N-{4-[4-(piperidinomethyl)pyridyl-2-oxy]butyl}-2-(3-furylmethylsulfonyl)acetamide

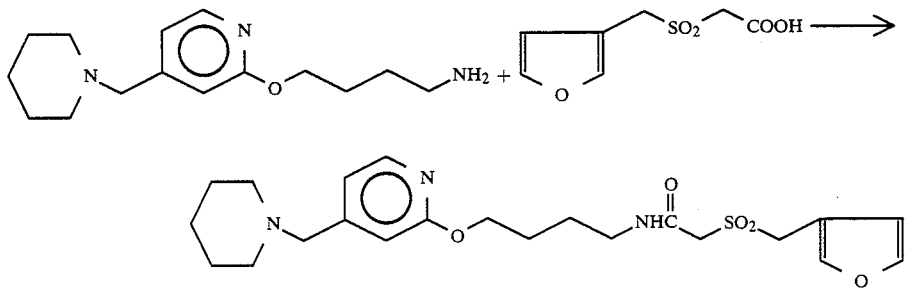

The captioned compound was obtained (yield 15%) by repeating Example 3 except that 0.65 mM of 4-[4-(piperidinomethyl)pyridyl-2-oxy]butanamine was used instead of the 4-[4-(piperidinomethyl)pyridyl-2-oxy]-cis-2-butenamine.

IR (cm$^{-1}$, film): 1678 (C=O), 1320, 1119 (SO$_2$).

$^1$H-NMR (δ, CDCl$_3$): 1.30–1.65 (6H, m), 1.65–1.90 (4H, m), 2.30–2.45 (4H, m), 3.38 (2H, dd, J=6.1 Hz), 3.40 (2H, s), 3.76 (2H, s), 4.30 (2H, t, J=6.1 Hz), 4.31 (2H, s), 6.59 (1H, 1.4 Hz), 6.70 (1H, s), 6.73 (1H, brs), 6.80 (1H, dd, J=5.4 Hz, 1.0 Hz), 7.43 (1H, d, J=1.4 Hz), 1.4 Hz), 7.65 (1H, s), 8.04 (1H, d, J=5.4 Hz).

Mass: as C$_{22}$H$_{31}$N$_3$O$_5$S:
Calculated: 449.1983.
Found: 449.1972.

EXAMPLE 23

Production of N-{4-[4-(4-methyl-1-piperazinylmethyl)pyridyl-2-oxy]-butyl}-2-(furfurylthio)acetamide

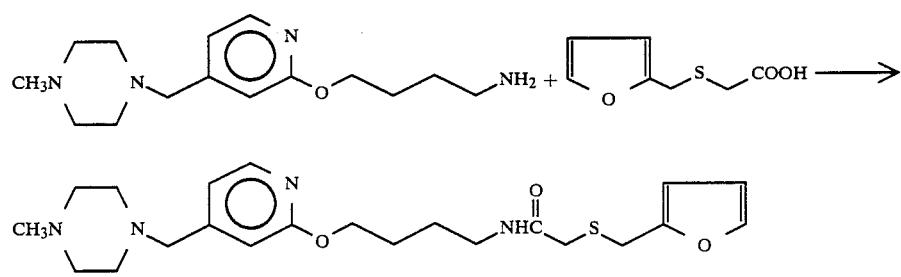

The captioned compound was obtained (yield 30%) by repeating Example 1 except that 0.65 mM of 4-[4-(4-methyl-1-piperazinylmethyl)pyridyl-2-oxy]butanamine was used instead of the 4-[4-(piperidinomethyl)pyridyl-2-oxy]-cis-2-butenamine.

IR (cm$^{-1}$, film): 1675 (C=O).

$^1$H-NMR (δ, CDCl$_3$): 1.68 (2H, tt, J=6.3 Hz, 6.3 Hz), 1.81 (2H, tt, J=6.3 Hz, 6.3 Hz), 2.31 (3H, s), 2.40–2.60 (8H, m), 3.22 (2H, s), 3.29 (2H, dt, J=6.3 Hz, 6.3 Hz), 3.48 (2H, s), 3.74 (2H, s), 4.30 (2H, t, J=6.3 Hz), 6.21 (1H, d, J=3.2 Hz), 6.30 (1H, dd, J=3.2 Hz, 1.4 Hz), 6.71 (1H, s), 6.80 (1H, brs), 6.86 (1H, d, J=5.4 Hz), 7.36 (1H, d, J=1.4 Hz), 8.05 (1H, d, J=5.4 Hz).

REFERENTIAL EXAMPLE 2

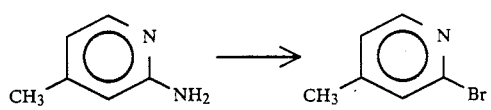

108.1 g of 2-amino-4-methylpyridine was dissolved in 500 ml of 47% hydrobromic acid, and the solution was cooled to 0° C. with a freezing mixture. Then, 500 g of bromine was added dropwise. A solution of 172.5 g of sodium nitrite in 500 ml of water was added dropwise while adjusting the reaction temperature to below 5° C. After the sodium nitrite solution was completely added, the mixture was stirred for 1 hour, and then a solution of 300 g of sodium hydroxide in 1 liter of water to render the solution basic. The solution was extracted with ethyl acetate. The organic layer was washed with water and dried. The solvent was evaporated. The residue was purified by distillation to give 126 g (yield 73%) of 2-bromo-4-methylpyridine.

Boiling point: 79°–81° C./4–5 mmHg $^1$H-NMR (δ, CDCl$_3$): 8.22 (1H, d, J=4.9 Hz), 7.33 (1H, s), 7.70 (1H, d, J=4.9 Hz), 2.34 (3H, s).

REFERENTIAL EXAMPLE 3

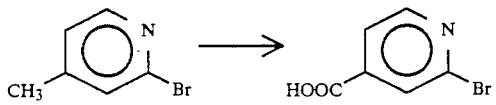

50 g of 2-bromo-4-methylpyridine was dissolved in 400 ml of conc. sulfuric acid, and under ice cooling, 87.2 g of chromic trioxide was added little by little. The mixture was stirred for 1 hour and put in ice water. The precipitated crystals were collected by filtration, and recrystallized from ethanol to give 48.8 g (yield 82%) of 2-bromo-4-pyridinecarboxylic acid having a melting point of 213.9° to 214.4° C.

REFERENTIAL EXAMPLE 4

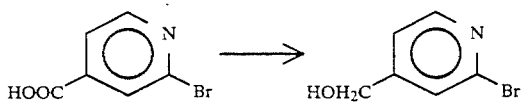

17.4 g of sodium borohydride was suspended in 1.6 liters of tetrahydrofuran, and the suspension was stirred by a mechanical stirrer. The suspension was cooled with ice-water, and 62.2 g of 2-bromo-4-pyridinecarboxylic acid was added little by little. The mixture was heated to room temperature, and stirred until evolution of hydrogen ceased. A solution of 75.8 ml of boron trifluoride etherate in 500 ml of tetrahydrofuran was added dropwise at room temperature for 3 hours. After the addition, the mixture was stirred for 20 hours. The reaction solution was cooled with ice-water, and acidified to a pH of 1 to 2 by adding 1.5N hydrochloric acid. Tetrahydrofuran was evaporated under reduced pressure. A 4N aqueous solution of sodium hydroxide was added to adjust the pH of the mixture to 10 to 11. It was extracted with ethyl acetate, and the organic layer was washed with a saturated aqueous solution of sodium chloride. The aqueous layer was further extracted with ethyl acetate twice. The organic layers were combined, and dried over anhydrous sodium sulfate. The dried product was concentrated under reduced pressure to give 51.3 g of 2-bromo-4-pyridinemethanol in a yield of 88%.

Melting point: 63.3° to 64.4° C. (diisopropyl ether)

$^1$H-NMR (δ, CDCl$_3$): 8.31 (1H, d, J=4.5 Hz), 7.38 (1H, s), 7.22 (1H, d, J=4.5 Hz), 4.76 (2H, s), 2.40–2.70 (1H, m).

IR (cm$^{-1}$, KBr): 3268, 1598, 1382, 1070

Mass: as C$_6$H$_6$BrO:

Found: 186.9638.

Calculated: 186.9633.

REFERENTIAL EXAMPLE 5

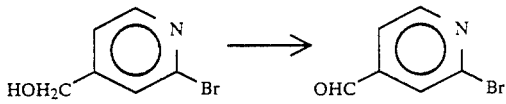

A mixture of 21.0 g of 2-bromo-4-pyridinemethanol, 32.3 g of N-bromosuccinimide and 23.1 g of anhydrous sodium carbonate was suspended in 600 ml of benzene, and heated under reflux (bath temperature 110° to 120° C.) for 4 hours. The mixture was cooled over an ice bath, and a saturated aqueous solution of sodium hydrogen carbonate was added to adjust its pH to 9 to 10. The insoluble matter was removed by filtration (by washing with ethyl acetate). The organic layer was separated, washed with a 10% aqueous solution of sodium thiosulfate and then with a saturated aqueous solution of sodium chloride, and dried over sodium sulfate. The solvent was evaporated to give 18.2 g (yield 88%) of 2-bromo-4-pyridinecarboxaldehyde.

Melting point: 52.6° to 53.5° C.

$^1$H-NMR (δ, CDCl$_3$): 10.03 (1H, s), 8.64 (1H, d, J=4.9 Hz), 7.90 (1H, s), 7.68 (1H, d, J=4.9 Hz).

IR (cm$^{-1}$, KBr) 1704, 1554, 1204.

Mass: as C$_6$H$_4$BrO:

Found: 184.9485.

Calculated: 184.9476.

REFERENTIAL EXAMPLE 6

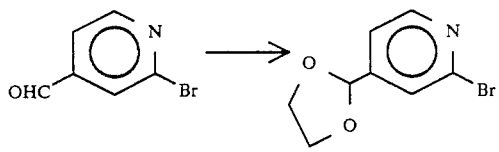

60 g of 2-bromo-4-pyridinecarboxaldehyde was dissolved in 600 ml of benzene, and 40 g of ethylene glycol and 6 g of p-toluenesulfonic acid were put in the solution. The mixture was heated under reflux for 18 hours while water was removed by using a Dean-Stark trap. After the reaction, the reaction mixture was made basic by adding ice and a saturated aqueous solution of sodium hydrogen carbonate. The organic layer was washed with water and dried. The solvent was evaporated. The residue was distilled to give 60 g (yield 82%) of 2-bromo-4-(1,3-dioxolan-2-yl)pyridine.

Boiling point: 121°–122° C./3 mmHg.

$^1$H-NMR (δ, CDCl$_3$): 8.39 (1H, d, J=5.5 Hz), 7.60 (1H, s), 7.34 (1H, d, J=5.5 Hz), 5.80 (1H, s), 4.07 (2H, d, J=12 Hz), 4.05 (2H, d, J=12 Hz).

IR (cm$^{-1}$, film): 2894, 1594, 1553, 1367, 1121, 1097

Mass: as C$_8$H$_8$BrNO:

Found: 228.9738.

Calculated: 228.9738.

EXAMPLE 24

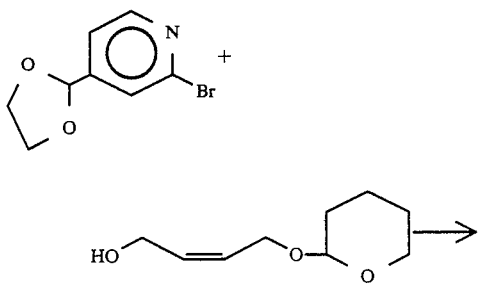

10 g of 2-bromo-4-(1,3-dioxolan-yl)pyridine, 9.7 g of 4-(2-oxytetrahydropyranyl)-cis-2-buten-1-ol (9.7 g), 7.0 g of powdery sodium hydroxide, 9.7 g of potassium carbonate and 1.3 g of tetra-n-butylammonium hydrogen sulfate were suspended in 150 ml of toluene, and the suspension was refluxed for 18 hours.

After cooling, the reaction mixture was diluted with benzene, washed with water, and dried. The solvent was evaporated to give 12.1 g (yield 87%) of 2-[4-(2-oxytetrahydropyranyl)-cis-2-buten-1-oxy]-4-(1,3-dioxolan-2-yl)pyridine.

$^1$H-NMR (δ, CDCl$_3$): 8.15 (1H, d, J=5.5 Hz), 6.96 (1H, d, J=5.5 Hz), 6.85 (1H, s), 5.79 (1H, s), 5.70–5.90 (2H, m), 4.93 (2H, d, J=5.4 Hz), 4.65–4.68 (1H, m), 4.37 (1H, dd, J=12.5, 5.4 Hz), 4.20 (1H, dd, J=12.5, 5.4 Hz), 4.04 (4H, d, J=2 Hz), 3.82–3.91 (1H, m), 3.46–3.56 (1H, m), 1.46–1.92 (6 H, m).

IR (cm$^{-1}$, film) 2952, 1618, 1566, 1316.
Mass: as C$_{17}$H$_{23}$NO$_5$:
Found: 321.1591.
Calculated 321.1577.

EXAMPLE 25

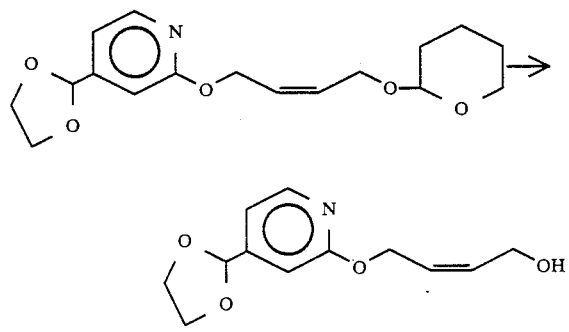

12.1 g of 2-[4-(2-oxytetrahydropyranyl)-cis-2-buten-1-oxy]-4-(1,3-dioxolan-2-yl)pyridine was dissolved in 250 ml of ethanol, and 1.5 g of pyridinium p-toluenesulfonate was added. The mixture was stirred at 55° C. (bath temperature) for 18 hours.

After the reaction, a saturated aqueous solution of sodium hydrogen carbonate was added to render the reaction mixture basic. The solvent was concentrated. The residue was taken into ethyl acetate, washed with water and dried. The solvent was evaporated to give 8.9 g of 4-[4-(1,3-dioxolan-2-yl)pyridyl-2-oxy]-cis-2-buten-1-ol quantitatively.

$^1$H-NMR (δ, CDCl$_3$); 8.10 (1H, d, J=4.5 Hz), 6.98 (1H, d, J=4.5 Hz), 6.86 (1H, s), 5.83–5.92 (1H, m), 5.78 (1H, s), 5:69–5.78 (1H, m), 5.01 (2H, d, J=7.4 Hz), 4.32 (2H, d, J=6.4 Hz), 4.01–4.08 (4H, m).

IR (cm$^{-1}$, film): 3424, 2896, 1620, 1566, 1426, 1316, 1032.
Mass: as C$_{12}$H$_{15}$NO$_4$:
Found: 237.0998.
Calculated: 237.1001.

EXAMPLE 26

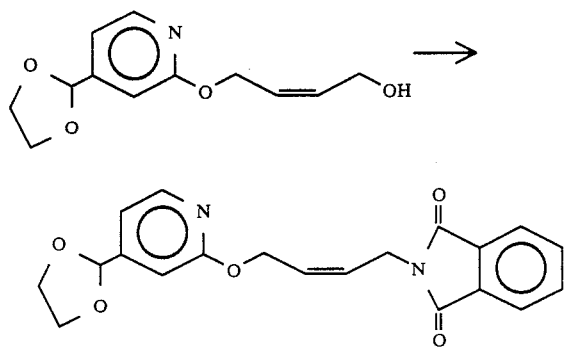

10 g of 4-[4-(1,3-dioxolan-2-yl)pyridyl-2-oxy]-cis-2-buten-1-ol and 6 g of triethylamine were dissolved in 250 ml of chloroform, and under ice cooling, 6 g of thionyl chloride was added dropwise.

Under the same conditions, the mixture was stirred for 1 hour. Ice and then a saturated aqueous solution of sodium hydrogen carbonate were added to render the solution basic. The organic layer was washed with water and dried, and the solvent was evaporated.

The residue, without purification, was immediately dissolved in 250 ml of acetonitrile, and 8 g of potassium phthalimide and 1.4 g of tetra-n-butylammonium hydrogen sulfate were added, and the mixture was refluxed overnight.

After cooling, the insoluble matter was removed from the reaction mixture by filtration, and the filtrate was concentrated. The concentrate was taken into ethyl acetate, washed with a 1N aqueous solution of sodium hydroxide and then with water, and dried. The solvent was evaporated.

The residue was recrystallized from ethanol to give 8 g (yield 53 %) of N-{4-[4-(1,3-dioxolan-2-yl)-pyridyl-2-oxy]-cis-2-butene}phthalimide.

Melting point: 96.9°–97.9° C.
$^1$H-NMR (δ, CDCl$_3$): 8.17 (1H, d, J=5.3 Hz), 7.85 (2H, dd, J=6.3, 3.7 Hz), 7.72 (2H, dd, J=6.3, 3.7 Hz), 6.98 (1H, d, J=5.3 Hz), 6.86 (1H, s), 5.88–5.96 (1H, m), 5.80 (1H, s), 5.64–5.74 (1H, m), 5.12 (2H, d, J=7.2 Hz), 4.47 (2H, d, J=7.2 Hz), 4.00–4.09 (4H, m).

IR (cm$^{-1}$, KBr): 2496, 1770, 1716, 1614, 1568, 1120, 1092.
Mass: as C$_{20}$H$_{18}$N$_2$O$_5$:
Found: 366.1221.
Calculated: 366.1216.

EXAMPLE 27

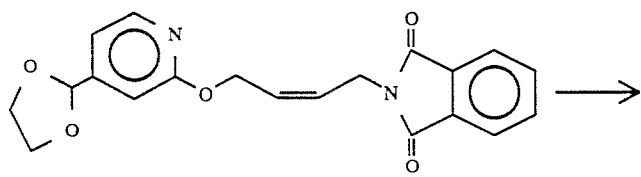

8.5 g of N-(4-[4-(1,3-dioxolan-2-yl)pyridyl-2-oxy}-cis-2-butene}phthalimide was dissolved in 200 ml of methanol, and 2.3 g of hydrazine hydrate was added. The mixture was refluxed for 10 hours. After cooling, the insoluble matter was removed from the reaction mixture by filtration, and the filtrate was concentrated. On standing, the residue crystallized to give 10.3 g (yield 78%) of 4-[4-(1,3-dioxolan-2-yl)pyridyl-2-oxy]-cis-2-buten-1-amine.

$^1$H-NMR (δ, CDCl$_3$): 8.15 (1H, d, J=4.8 Hz), 6.97 (1H, d, J=4.8 Hz), 6.85 (1H, s), 5.78 (1H, s), 5.68–5.76 (2H, m), 4.90 (2H, d, J=4.8 Hz), 4.01–4.07 (4H, m), 3.45 (2H, d) J=4.8 Hz).

IR (cm$^{-1}$, KBr): 3068, 1666, 1082.

EXAMPLE 28

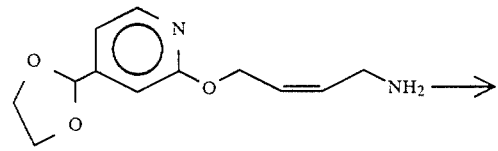

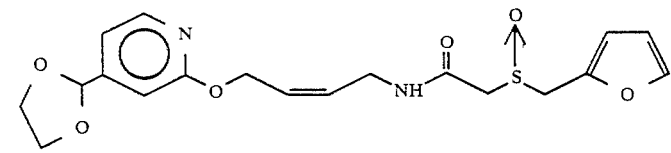

13.5 g of p-nitrophenyl furfurylsulfinylacetate was suspended in 300 ml of tetrahydrofuran, and under ice cooling, a solution of 10.3 g of 4-[4-(1,3-dioxolan-2-yl)-pyridyl-2-oxy]-cis-2-buten-1-amine in 100 ml of tetrahydrofuran was added dropwise. The temperature was returned to room temperature one hour later, and the mixture was stirred overnight.

The solution was concentrated. The residue was taken into ethyl acetate, washed with a 1N aqueous solution of sodium hydroxide and water, and dried. The solvent was evaporated to give 16.1 g (yield 91%) of N-{4-[4-(1,3-dioxolan-2-yl)pyridyl-2-oxy]-cis-2-butenyl}-2-(furfurylsulfinyl)acetamide.

$^1$H-NMR (δ, CDCl$_3$): 8.15 (1H, d, J=5.5 Hz), 7.44 (1H, d, J=2.4 Hz), 7.10–7.20 (1H, br-s), 6.98 (1H, d, J=5.5 Hz), 6.47 (1H, d, J=2.8 Hz), 6.39 (1H, dd, J=2.4, 2.8 Hz), 5.79–5.90 (1H, m), 5.78 (1H, s), 5.63–5.72 (1H, m), 4.95 (2H, d, J=6.9 Hz), 4.27 (1H, d, J=14.2 Hz), 4.18 (1H, d, J=14.2 Hz), 4.10 (2H, t, J=6.6 Hz), 4.01–4.07 (4H, m), 3.59 (1H, d, J=14.2 Hz), 3.34 (1H, d, J=14.2 Hz).

IR (cm$^{-1}$, film): 1660, 1618, 1566, 1310, 1034.

Mass: as C$_{19}$H$_{22}$N$_2$O$_6$S:
Found: 406.1208.
Calculated: 406.1199.

EXAMPLE 29

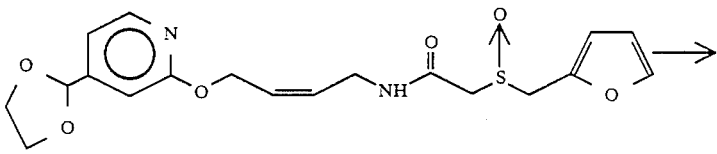

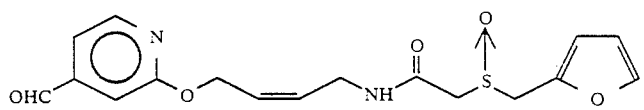

10.0 g of N-{(4-[4-(1,3-dioxolan-2-yl)pyridyl-2-oxy]-cis-2-butenyl}-2-(furfurylsulfinyl)acetamide was dissolved in 200 ml of a 1:1 mixture of water and acetone, and 5.6 g of p-toluenesulfonic acid was added. The mixture was refluxed for 18 hours. After cooling, a saturated aqueous solution of sodium hydrogen carbonate was added to the reaction mixture to make it basic, and the mixture was concentrated. The concentrate was taken into ethyl acetate, washed with water, and dried, and the solvent was evaporated. The residue was subjected to column chromatography (1% methanol-chloroform) to give 4.6 g (yield 52%) of N-[4-(4-formyl-2-pyridyloxy)-cis-2-butenyl]-2-(furfurylsulfinyl)acetamide.

Melting point: 67.6°-69.9° C.

$^1$H-NMR (δ, CDCl$_3$): 10.00 (1H, s), 8.36 (1H, d, J=4.6 Hz), 7.45 (1H, d, J=3 Hz), 7.30 (1H, d, J=4.6 Hz), 7.16 (1H, s), 7.08 (1H, br-s), 6.47 (1H, d, J=3.5 Hz), 6.40 (1H, dd, J=3.5, 3.0 Hz), 5.82-5.92 (1H, m), 5.66-5.76 (1H, m), 5.00 (2H, d, J=6.4 Hz), 4.27 (1H, d, J=14.3 Hz), 4.18 (1H, d, J=14.3 Hz), 4.12 (2H, t, J=6.3 Hz), 3.59 (1H, d, J=14.1 Hz), 3.34 (1H, d, J=14.1 Hz).

IR (cm$^{-1}$, KBr): 3236, 1712, 1624, 1564, 1036.

Mass: as C$_{17}$H$_{18}$N$_2$O$_5$S:
Found: 362.0934.
Calculated: 362.0937.

EXAMPLE 30

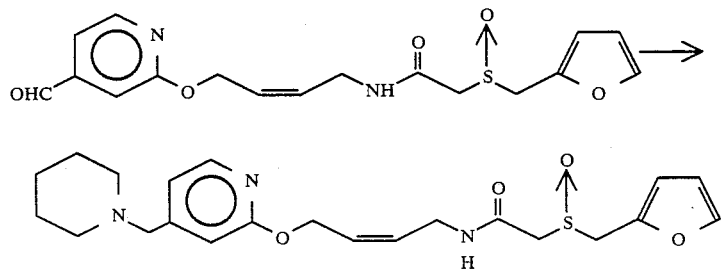

4.0 g of N-[4-(4-formyl-2-pyridyloxy)-cis-2-butenyl]-2-(furfurylsulfinyl)acetamide was dissolved in 100 ml of ethanol, and under ice cooling, 2.0 g of piperidine was added. The mixture was stirred. Three hours later, 0.5 g of sodium borohydride was added under ice cooling, and the mixture was stirred. Acetic acid was added to decompose the hydride, and the solution was concentrated.

The residue was taken into ethyl acetate and extracted twice with 20% acetic acid. The acetic acid layer was washed four times with ethyl acetate, made basic with potassium carbonate and extracted with ethyl acetate. The organic layer was washed with water, and dried. The solvent was evaporated. The residue was recrystallized from ether-hexane to give 2.2 g (yield 46%) of N-{4-[4-(piperidinomethyl)pyridyl-2-oxy]-cis-2-butenyl}-2-(furfurylsulfinyl)acetamide.

Melting point: 92.7°-94.9° C.

$^1$H-NMR (δ, CDCl$_3$): 1.40-1.50 (2H, m), 1.50-1.65 (4H, m), 2.30-2.45 (4H, m), 3.34 (1H, d, J=14.2 Hz), 3.40 (2H, s), 3.96 (1H, d, J=14.2 Hz), 4.15 (2H, dd, J=6.1 Hz, 6.1 Hz), 4.14 (1H, d, J=14.2 Hz), 4.38 (1H, d, J=14.2 Hz), 4.93 (2H, t, J=6.1 Hz), 5.60-5.75 (1H, m), 5.80-5.90 (1H, m), 6.40 (1H, dd, J=3.1 Hz, 1.6 Hz), 6.47 (1H, d, J=3.1 Hz), 6.73 (1H, s), 6.87 (1H, d, J=5.1 Hz), 7.15-7.25 (1H, brs), 7.44 (1H, d, J=1.6 Hz), 8.04 (1H, d, J=5.1 Hz).

IR (cm$^{-1}$, film): 1645 (C=O), 1041 (S—O).

Mass: as C$_{22}$H$_{29}$O$_4$S:
Found: 431.1883.
Calculated: 431.1879.

REFERENTIAL EXAMPLE 7

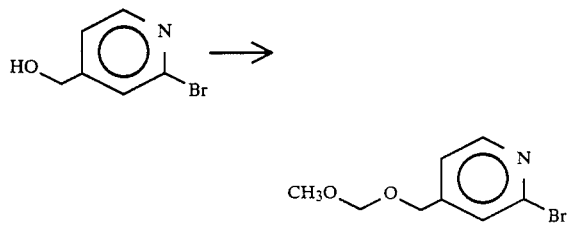

70 ml of 2-bromo-4-pyridinemethanol, 70 ml of dimethoxymethane and 2.15 g of p-toluenesulfonic acid monohydrate were suspended in 300 ml of benzene. The suspension was passed through a Soxhlet extractor containing 25 g of 3 Å molecular sieves, and refluxed for 20 hours. After cooling, the reaction mixture was washed with a saturated aqueous solution of sodium hydrogen carbonate and water, dried, and concentrated under reduced pressure. The residue was distilled to give 13.2 g (yield 50%) of 2-bromo-4-(methoxymethoxymethyl)pyridine.

Boiling point: 118°-125° C./3 mmHg.

$^1$H-NMR (δ, CDCl$_3$): 8.33 (1H, d, J=4.8 Hz), 7.51 (1H, s), 7.22 (1H, dd, J=4.8, 2.1 Hz), 4.73 (2H, s), 4.59 (2H, s), 3.41 (3H, s),

IR (cm$^{-1}$, film): 2950, 1600, 1550, 1470, 1390.

Mass: as C$_8$H$_{10}$BrNO$_2$:
Found: 232.9880.
Calculated: 232.9876.

REFERENTIAL EXAMPLE 8

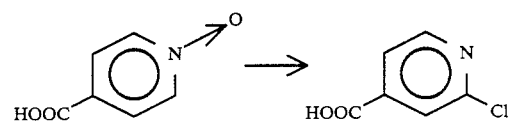

87 g of isonicotinic acid N-oxide, 350 ml of phosphorus oxychloride and 192 g of phosphorus pentachloride were mixed and refluxed for 3 hours. The reaction mixture was poured into water and left to stand overnight. The resulting precipitate was collected by filtration, and recrystallized from ethanol to give 65 g (66 %) of 2-chloro-4-pyridinecarboxylic acid.

Melting point: 228.1°-228.7° C.

IR (cm$^{-1}$, KBr): 1718, 1604, 1566, 1458, 1372.

Mass: as C$_6$H$_4$NO$_2$Cl:
Found: 156.9940.
Calculated: 156.9931.

REFERENTIAL EXAMPLE 9

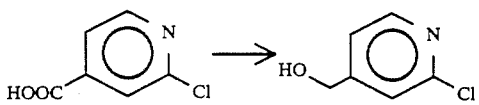

35.59 g of sodium borohydride was suspended in 3 liters of tetrahydrofuran, and the suspension was stirred by a mechanical stirrer. The suspension was cooled with ice water, and 98.83 g of 2-chloro-4-pyridinecarboxylic acid was added little by little. The mixture was heated to room temperature, and stirred until evolution of hydrogen ceased. A solution of 148 ml of boron trifluoride etherate in 1000 ml of tetrahydrofuran was added dropwise at room temperature for 3 hours. After the addition, the mixture was stirred for 20 hours. The reaction solution was cooled with ice water, and adjusted to pH 1 to 2 with 1.5N hydrochloric acid. The tetrahydrofuran was evaporated under reduced pressure, and a 4N aqueous solution of sodium hydroxide was added to adjust the pH of the mixture to 10 to 11. The solution was then extracted with ethyl acetate and the organic layer was washed with a saturated aqueous solution of sodium chloride. The aqueous layer was further extracted with ethyl acetate twice, and the organic layers were washed with a saturated aqueous solution of sodium chloride. The organic layers were combined, dried over anhydrous sodium sulfate, and concentrated under reduced pressure to give 75.0 g (yield 83%) of 2-chloro-4-pyridinemethanol.

Melting point: 65.7°–66.4° C.

$^1$H-NMR ($\delta$, CDCl$_3$): 8.30 (1H, d, J=4.6 Hz), 7.37 (1H, s), 7.22 (1H, d, J=4.6 Hz), 4.76 (2H, s), 2.70–2.85 (1H, br-s).

IR (cm$^{-1}$, film) 3284, 1600, 1394.

REFERENTIAL EXAMPLE 10

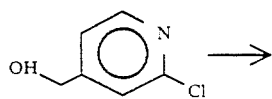

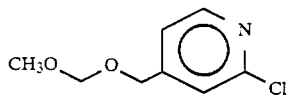

4.30 g of 2-chloro-4-pyridinemethanol, 20 ml of dimethoxymethane and 0.57 g of p-toluenesulfonic acid monohydrate were suspended in 200 ml of benzene. The suspension was passed through a Soxhlet extractor containing 25 g of 2 Å molecular sieves, and refluxed for 20 hours. After cooling, the reaction solution was washed with a saturated solution of sodium hydrogen carbonate and water, dried, and concentrated under reduced pressure. The residue was distilled to give 4.0 g (yield 71%) of 2-chloro-4-(methoxymethoxymethyl)-pyridine.

Boiling point: 118°–120° C./5 mmHg.

$^1$H-NMR ($\delta$, CDCl$_3$): 8.35 (1H, d, J=5.6 Hz), 7.36 (1H, s), 7.20 (1H, d, J=5.6 Hz), 4.74 (2H, s), 4.61 (2H, s), 3.41 (3H, s).

EXAMPLE 31

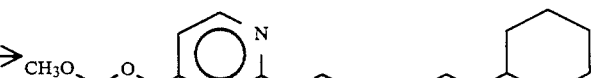

4.8 g of sodium hydride having a purity of 60% was suspended in 50 ml of tetrahydrofuran and 5 ml of dimethylformamide, and under ice cooling, a solution of 13.9 g of 2-bromo-4-(methoxymethoxymethyl)pyridine and 13.25 g of 4-(2-oxytetrahydropyranyl)-cis-2-buten-1-ol in 200 ml of tetrahydrofuran was added dropwise. The mixture was refluxed for 18 hours. After cooling, 10 ml of water was added, and the mixture was concentrated under reduced pressure. The residue was taken into benzene, and filtered through Celite. The filtrate was washed with water and dried, and the solvent was evaporated to give 16 g (yield 82%) of 2-[4-(2-oxytetrahydropyranyl)-cis-2-buten-1-oxy]-4-(methoxymethoxymethyl)pyridine.

$^1$H-NMR ($\delta$, CDCl$_3$): 8.10 (1H, d, J=5.4 Hz), 6.84 (1H, d, J=5.4 Hz), 6.74 (1H, s), 5.84 (2H, s), 4.92 (2H, d, J=6 Hz), 4.71 (2H, s), 4.66 (1H, t, J=3.6 Hz), 4.55 (2H, s), 4.37 (1H, dd, J=11.7, 6.3 Hz), 4.19 (1H, dd, J=11.7, 6.3 Hz), 3.87 (1H, m), 3.55 (1H, m), 3.40 (3H, s), 1.49–1.80 (6H, m).

IR (cm$^{-1}$, film): 2950, 1620, 1570, 1450, 1320.

Mass: as C$_{17}$H$_{25}$NO$_5$:
Found: 323.1745.
Calculated: 323.1733.

EXAMPLE 32

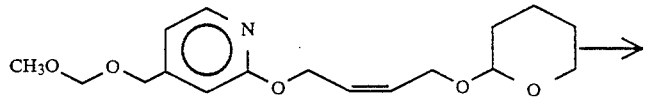

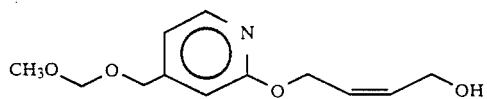

16 g of 2-[4-(2-oxytetrahydropyranyl)-cis-2-buten-1-oxy]-4-(methoxymethoxymethyl)pyridine was dissolved in 300 ml of ethanol, and 1.3 g of pyridinium p-toluenesulfonate was added. The mixture was stirred for 18 hours at 60° C. (bath temperature). After the reaction, a saturated aqueous solution of sodium hydrogen carbonate was added to render the reaction mixture alkaline, and then the reaction mixture was concentrated under reduced pressure. The residue was taken into ethyl acetate, washed with water, and dried. The solvent was evaporated to give 11.28 g (yield 95%) of 4-[4-(methoxymethoxymethyl)pyridyl-2-oxy]-cis-2-buten-1-ol.

$^1$H -NMR (δ, CDCl$_3$): 8.05 (1H, d, J=5.4 Hz), 6.85 (1H, d, J=5.4 Hz), 6.76 (1H, s), 5.89 (1H, m), 5.76 (1H, m), 5.01 (2H, d, J=6.9 Hz), 4.71 (2H, s), 4.56 (2H, s), 4.32 (2H, d, J=6.0 Hz), 3.40 (3H, s).

IR (cm$^{-1}$, film): 3400, 2950, 1620, 1560, 1420, 1320.
Mass: as C$_{12}$H$_{17}$NO$_4$:
Found: 239.1161.
Calculated: 239.1158.

EXAMPLE 33

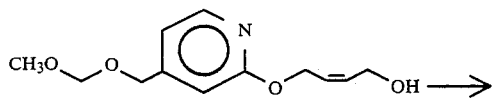

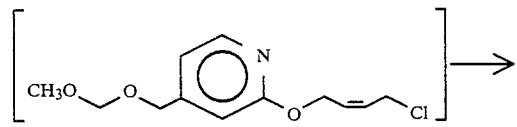

2 g of 4-[4-(methoxymethoxymethyl)pyridyl-2-oxy]-cis-2-buten-1-ol was dissolved in 30 ml of dichloromethane, and 3 g of anhydrous potassium carbonate was suspended in the solution Under ice cooling, a solution of 1.1 g of thionyl chloride in 5 ml of dichloromethane was added dropwise. Under the same conditions, the mixture was stirred for 1 hour. The insoluble matter was removed by filtration, and the solution was concentrated under reduced pressure. The residue was dissolved in 100 ml of toluene, and 2.3 g of potassium phthalimide and 305 g of tetra-n-butylammonium hydrogen sulfate were suspended in the solution. The suspension was refluxed for 18 hours. After cooling, the insoluble matter was removed by filtration, and the residue was diluted with benzene, washed with a 1N aqueous solution of sodium hydroxide and water, and dried. The solvent was evaporated to give 97 g (yield 97%) of N-{4-[4-(methoxymethoxymethyl)pyridyl-2-oxy]-cis-2-butenyl}phthalimide.

Melting point: 69.2°–70.1 ° C. (ethanol-ethyl ether)
$^1$H -NMR (δ, CDCl$_3$): 8.13 (1H, d, J=5.4 Hz), 7.84 (2H, m), 7.72 (2H, m), 6.85 (1H, d, J=5.4 Hz), 6.76 (1H, s), 5.92 (1H, m), 5.68 (1H, m), 5.11 (2H, d, J=6.6 Hz), 4.71 (2H, s). 4.56 (2H, s), 4.47 (2H, d, J=7.2 Hz), 3.41 (3H, s).

IR (cm$^{-1}$, KBr): 2960, 1720, 1630, 1570, 1400, 1320.
Mass: as C$_{20}$H$_{20}$N$_2$O$_5$:
Found: 368.1360.
Calculated: 368.1372.

EXAMPLE 34

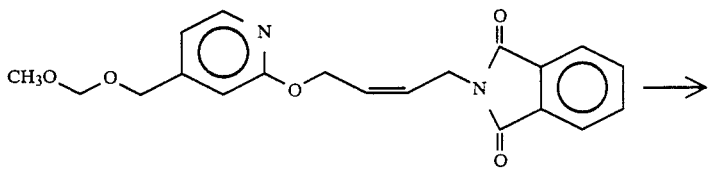

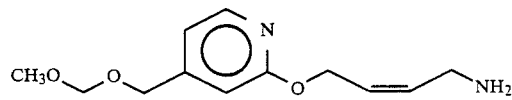

3.285 g of N-{4-[4-(methoxymethoxymethyl)-pyridyl-2-oxy]-cis-2-butenyl}phthalimide was dissolved in 100 ml of methanol, and 1.48 g of hydrazine monohydrate was added. The mixture was refluxed for 3 hours. The reaction mixture was concentrated under reduced pressure. The residue (crystal) was washed with dichloromethane, and the filtrate was concentrated under reduced pressure. The residue was taken into ethyl acetate, washed with water, and dried. The solvent was evaporated to give 1.84 g (yield 86%) of 1-amino-4-[4-methoxymethoxymethyl)pyridyl-2-oxy]-cis-2-butene.

$^1$H -NMR (δ, CDCl$_3$): 8.10 (1H, d, J=4.5 Hz), 6.85 (1H, d, J=4.5 Hz), 6.75 (1H, s), 5.74 (2H, m), 4.89 (2H, m), 4.71 (2H, s), 4.55 (2H, s), 3.45 (2H, m), 3.40 (3H, s), 1.49 (2H, br-s).

IR (cm$^{-1}$, film): 3400, 3300, 2950, 1620, 1570, 1430, 1320.
Mass: as C$_{12}$H$_{18}$N$_2$O$_3$:
Found: 238.1294.
Calculated: 238.1317.

EXAMPLE 35

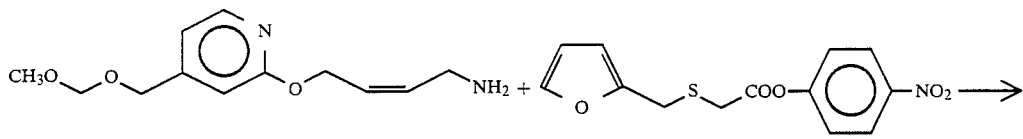

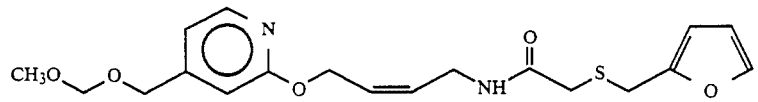

1.7 g of 1-amino-4-[4-(methoxymethoxymethyl)-pyridyl-2-oxy]-cis-2-butene was dissolved in 100 ml of tetrahydrofuran, and 2.34 g of p-nitrophenyl furfurylthioacetate was added. The mixture was stirred overnight at room temperature. The reaction solution was concentrated under reduced pressure. The residue was taken into ethyl acetate, washed with a 1N aqueous solution of sodium hydroxide and water, and dried. The solvent was evaporated to give 2.5 g (yield 89%) of N-{4-[4-methoxymethoxymethyl)pyridyl-2-oxy]-cis-2-butenyl}-2-(furfurylthio)acetamide.

$^1$H -NMR ($\delta$, CDCl$_3$): 8.12 (1H, d, J=4.2 Hz), 7.36 (1H, m), 6.86 (2H, d, J=4.2 Hz), 6.77 (1H, s), 6.29 (1H, dd, J=3.3, 1.8 Hz), 6.20 (1H, d, J=3.9 Hz), 5.85 (1H, m), 5.62 (1H, m), 4.93 (2H, d, J=6.3 Hz), 4.72 (2H, s), 4.56 (2H, s), 3.99 (2H, t, J=5.4 Hz), 3.74 (2H, s), 3.41 (3H, s), 3.22 (2H, s).

IR (cm$^{-1}$, film): 3350, 2950, 1660, 1620, 1560, 1420.
Mass: as C$_{19}$H$_{24}$N$_2$O$_5$S:
Found: 392.1402.
Calculated: 392.1405.

EXAMPLE 36

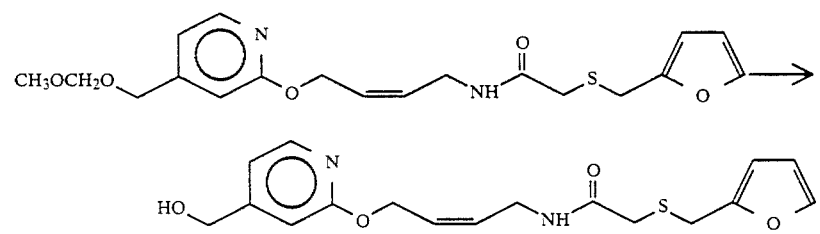

200 mg of N-{4-[4-(methoxymethoxymethyl)-pyridyl-2-oxy]-cis-2-butenyl}-2-(furfurylthio)acetamide was dissolved in 15 ml of methanol, and 10 mg of p-toluenesulfonic acid monohydrate was added. The mixture was refluxed, and after the reaction, the reaction mixture was cooled and made alkaline by adding a saturated aqueous solution of sodium hydrogen carbonate. The mixture was then concentrated under reduced pressure. The residue was taken into ethyl acetate, washed with water, and dried. The solvent was then evaporated. The residue was subjected to column chromatography (moving phase: benzene/ethyl acetate) to give 87 mg (yield 50%) of N-{4-[4-(hydroxymethyl)pyridyl-2-oxy]-cis-2-butenyl}-2-(furfurylthio)acetamide.

$^1$-NMR ($\delta$, CDCl$_3$): 8.11 (1H, d, J=60 Hz), 7.35 (1H, d, 1.5 Hz), 6.86 (2H, d, J=4.2 Hz), 6.79 (1H, s), 6.29 (1H, dd, J=3.3, 1.5 Hz), 5.84 (1H, m), 5.60 (1H, m), 4.93 (2H, d, J=5.7 Hz), 4.68 (2H, s), 3.98 (2H, t, J=6.6 Hz), 3.73 (2H, s), 3.22 (2H, s).

IR (cm$^{-1}$, film): 3400, 2950, 1660, 1620, 1560, 1420 1400.

Mass: as C$_{17}$H$_{20}$N$_2$O$_4$S:
Found: 348.1140.
Calculated: 348.1143.

EXAMPLE 37

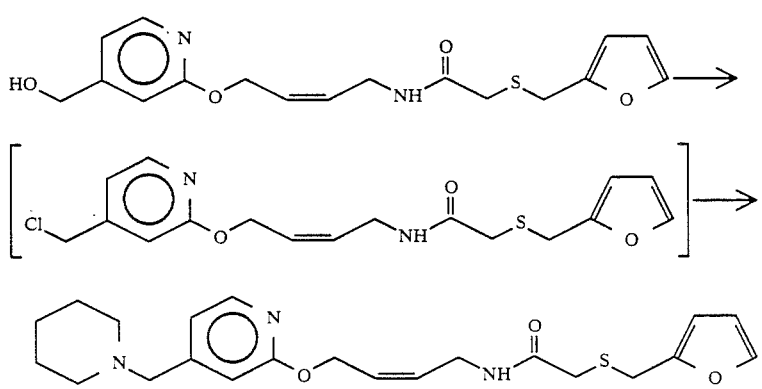

900 mg of N-{4-[4-(hydroxymethyl)pyridyl-2-oxy]-cis-2-butenyl}-2-(furfurylthio)acetamide and 834 mg of triethylamine were dissolved in 20 ml of chloroform, and a solution of 946 mg of methanesulfonyl chloride in 5 ml of chloroform was added dropwise under ice cooling. The mixture was stirred for 1 hour, and the reaction mixture was washed with a saturated aqueous solution of sodium hydrogen carbonate and water, and dried. The solvent was evaporated. The residue was dissolved in ethanol and added to 1.17 g of piperidine under ice cooling. The mixture was refluxed for 6 hours. The reaction mixture was concentrated under reduced pressure, and the residue was taken into ethyl acetate and extracted with a 10% aqueous solution of acetic acid. Potassium carbonate (solid) was added to the aqueous layer to make it alkaline, and the alkaline layer was extracted with ethyl acetate. The organic layer was washed with water, and dried, and the solvent was evaporated to give 820 mg (79%) of N-{4-[4-(piperidinomethyl)pyridyl-2-oxy]-cis-2-butenyl}-2-(furfurylthio)acetamide.

$^1$H -NMR (δ, CDCl$_3$): 8.06 (1H, d, J=4.2 Hz), 7.35 (1H, d, J=1.8 Hz), 6.88 (2H, d, J=4.2 Hz), 6.74 (1H, s), 6.29 (1H, dd, J=4.2, 1.8 Hz), 6.20 (1H, d, J=1.8 Hz), 5.86 (1H, m), 5.64 (1H, m), 4.91 (2H, d, J=7.2 Hz), 3.99 (2H, t, J=6.0 Hz), 3.74 (2H, s), 3.41 (2H, s), 3.22 (2H, s), 2.37 (4H, m), 1.58 (4H, m), 1.44 (2H, m).

IR (cm$^{-1}$, film): 3350, 2950, 1670, 1620, 1570, 1430 1420 1310.

Mass: as C$_{22}$H$_{29}$N$_3$O$_3$S:
Found: 415.1927.
Calculated: 415.1929.

EXAMPLE 38

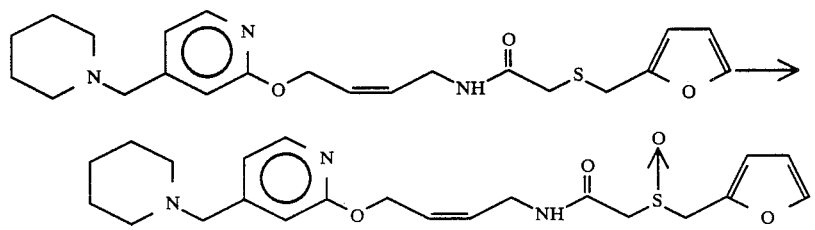

810 mg of N-{4-[4-(piperidinomethyl)pyridyl-2-oxy]-cis-2-butenyl}-2-(furfurylthio)acetamide was dissolved in 30 ml of dichloromethane, and the solution was cooled with ice-sodium chloride. A solution of 493 mg of m-chloroperbenzoic acid in 15 ml of dichloromethane was added dropwise. Under the same conditions, the mixture was stirred for 15 minutes. The reaction mixture was washed with a cold saturated aqueous solution of sodium hydrogen carbonate and water and dried. The solvent was evaporated to give 387 mg (yield 45%) of N-{4[4-(piperidinomethyl)pyridyl-2-oxy]-cis-2-butenyl}-2-(furfurylsulfinyl)acetamide.

Melting point: 92.7°-94.9° C.

$^1$H -NMR (δ, CDCl$_3$): 8.04 (1H, d, J=5.1 Hz), 7.44 (1H, d, J=1.6 Hz), 7.15-7.25 (1H, br-s), 6.73 (1H, s), 6.47 (1H, d, J=5.1 Hz), 6.40 (1H, dd, J=3.1, 1.6 Hz), 5.80-5.90 (1H, m), 5.60-5.75 (1H, m), 4.93 (2H, t, J=6.1 Hz), 4.38 (1H, d, J=14.2 Hz), 4.15 (2H, dd, J=6.1, 6.1 Hz), 4.14 (1H, d, J=14.2 Hz), 3.69 (1H, d, J=14.2 Hz), 3.40 (2H, s), 3.34 (1H, d, J=14.2 Hz), 2.30-2.45 (4H, m), 1.50-1.65 (4H, m), 1.40-1.50 (2H, m).

IR (cm$^{-1}$, KBr): 3350, 2950, 1645, 1620, 1530, 1410, 1290, 1041.

Mass: as C$_{22}$H$_{29}$N$_3$O$_4$S:
Found: 431.1883.
Calculated 431.1879.

REFERENTIAL EXAMPLE 11

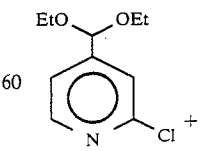

69.0 g of 2-chloro-4-pyridinemethanol, 128.3 g of N-bromosuccinimide and 101.9 g of anhydrous sodium carbonate were suspended in 1.8 liters of benzene, and refluxed for 4 hours. After cooling, a saturated aqueous solution of sodium hydrogen carbonate was added little by little with stirring until bubbling ceased. The insoluble matter was removed by filtration. The organic layer was separated, washed with a 10% aqueous solution of sodium thiosulfate once and then a saturated aqueous solution of sodium chloride twice, and dried. The solvent was evaporated to give 64.3 g (yield 95%) of 2-chloro-4-pyridinecarboxaldehyde.

$^1$H -NMR (δ, CDCl$_3$): 7.66 (1H, d, J=4.7 Hz), 7.76 (1H, s), 8.66 (1H, d, J=4.7 Hz), 10.06 (1H, s).

IR (cm$^{-1}$, film): 2860, 1712, 1592, 1558.

REFERENTIAL EXAMPLE 12

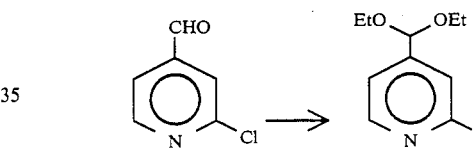

60 g of 2-chloro-4-pyridinecarboxaldehyde and 90 g of ethyl orthoformate were dissolved in 600 ml of ethanol, and 7 g of p-toluenesulfonic acid was added. The mixture was refluxed for 1 hour. After cooling, the reaction solution was concentrated. The concentrate was taken into ethyl acetate, washed with a saturated aqueous solution of sodium hydrogen carbonate and then a saturated aqueous solution of sodium chloride, and dried. The solvent was then evaporated. The residue was distilled under reduced pressure to give 75 g (yield 82%) of 2-chloro-4-diethoxymethylpyridine.

Boiling point: 102°-103° C./2 mmHg $^1$-NMR (δ, CDCl$_3$): 1.26 (6H, t, J=7.2 Hz), 3.50-3.65 (4H, m), 5.48 (1H, s), 7.32 (1H, d, J=5.4 Hz), 7.46 (1H, s), 8.39 (1H, d, J=5.4 Hz).

IR (cm$^{-1}$, film): 2984, 1596, 1556.

EXAMPLE 39

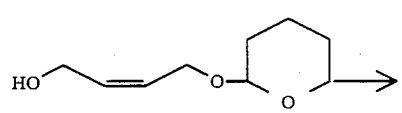

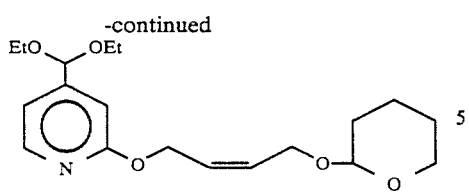

20 g of 2-chloro-4-diethoxymethylpyridine and 31.32 g of 4-(2-oxytetrahydropyranyl)-cis-2-buten-1-ol were dissolved in 500 ml of tetrahydrofuran, and 10 ml of dimethylformamide was added. Under ice cooling, oily sodium hydride (9.28 g, 60% assay) was suspended in the solution. The temperature of the solution was returned to room temperature, and then it was gradually heated to 80° C. and further refluxed for 18 hours. After cooling, water was added under ice cooling and the solution was concentrated. The residue was diluted with benzene, and the insoluble matter was removed by filtration through Celite. The organic layer as the filtrate was separated, and the aqueous layer was again extracted with benzene. The organic layers were combined, washed with a saturated aqueous solution of sodium chloride, and dried. The solvent was evaporated to give 49.62 g of 2-[4-(2-oxytetrahydropyranyl)-cis-2-buten-1-oxy]-4-(diethoxymethyl)pyridine.

Yield: quantitative $^1$H -NMR (δ, CDCl$_3$): 1.24 (6H, t, J=7.2 Hz), 1.40–1.90 (6H, m), 3.40–3.70 (5H, m), 3.85–3.95 (1H, m), 4.20–4.30 (1H, m), 4.40–4.50 (1H, m), 4.65–4.70 (1H, m), 4.92 (2H, d, J=6.4 Hz), 5.44 (1H, s), 5.75–5.95 (2H, m), 6.87 (1H, s), 6.98 (1H, d, J=5.5 Hz), 8.13 (1H, d, J=5.5 Hz).

IR (cm$^{-1}$, film): 2984, 1616, 1566.

EXAMPLE 40

49.62 g of 2-[4-(2-oxytetrahydropyranyl)-cis-2-buten-1-oxy]-4-(diethoxymethyl)pyridine was dissolved in 500 ml of ethanol, and 2.64 g of p-toluenesulfonic acid was added. The mixture was stirred for 3 hours. After cooling, a saturated aqueous solution of sodium hydrogen carbonate was added under ice cooling to render the solution basic, and then the solution was concentrated. The residue was extracted twice with ethyl acetate. The extracts were washed with a saturated aqueous solution of sodium chloride, dried and concentrated to give 29 g of 4-[4-(diethoxymethyl)pyridyl-2-oxy]-cis-2-buten-1-ol.

Yield: quantitative $^1$H -NMR (δ, CDCl$_3$): 1.24 (6H, t, J=7.4 Hz), 3.50–3.70 (4H, m), 4.33 (2H, d, J=6.5 Hz), 5.01 (2H, d, J=6.8 Hz), 5.43 (1H, s), 5.70–5.80 (1H, m), 5.90–6.00 (1H, m), 6.88 (1H, s), 6.99 (1H, d, J=5.3 Hz), 8.07 (1H, d, J=5.3 Hz).

IR (cm$^{-1}$, film): 3416, 1616, 1586.

Mass: as C$_{14}$H$_{21}$NO$_4$:
Calculated: 267.1471.
Found: 267.1477.

EXAMPLE 41

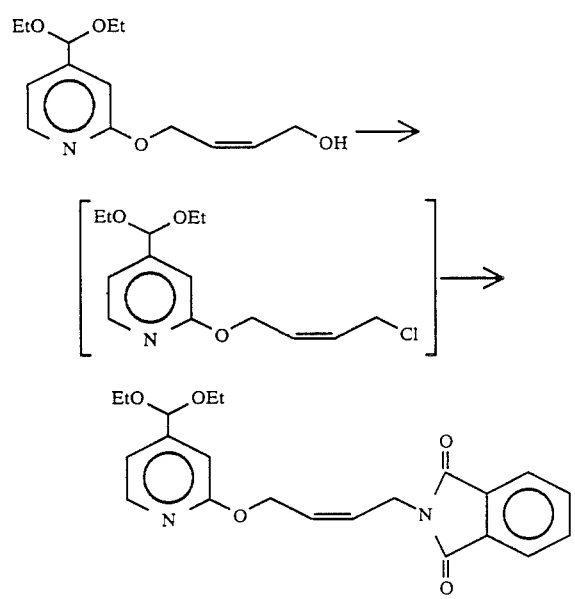

29 g of 4-[4-(diethoxymethyl)pyridyl-2-oxy]-cis-2-buten-1-ol was dissolved in 500 ml of methylene chloride, and 12.2 g of anhydrous potassium carbonate was suspended in the solution. Under ice cooling, a solution of 13.2 g of thionyl chloride in 100 ml of methylene chloride was added dropwise. The mixture was stirred for 1 hour, and the solid was separated by filtration. The filtrate was concentrated and the residue was dissolved in 800 ml of toluene. 26.5 g of potassium phthalimide, 0.9 g of anhydrous potassium carbonate and 3.1 g of tetra-n-butylammonium hydrogensulfate were suspended. With vigorous stirring, the mixture was refluxed for 20 hours. After cooling, the insoluble matter was separated by filtration and washed well with ethyl acetate. The filtrate and the washing were combined and washed with water. The aqueous layer was extracted with ethyl acetate. The organic layers were combined, washed with a cold 1N-solution of sodium hydroxide three times and then with a saturated aqueous solution of sodium chloride once, and dried. The solvent was evaporated to give 41.05 g of N-{4-[4-(diethoxymethyl)pyridyl-2-oxy]-cis-2-butene)phthalimide.

Yield: quantitative $^1$H -NMR (δ, CDCl$_3$): 1.24 (6H, t, J=7.2 Hz), 3.50–3.70 (4H, m), 4.57 (2H, d, J=6.2 Hz), 5.12 (2H, d, J=6.5 Hz), 5.44 (1H, s), 5.60–5.70 (1H, m), 5.90–6.00 (1H, m), 6.89 (1H, s), 6.98 (1H, d, J=5.2 Hz), 7.70–7.80 (2H, m), 7.80–7.90 (2H, m), 8.15 (d, J=5.2 Hz).

IR (cm.$^{-1}$): 1770, 1716, 1614.

Mass: as C$_{22}$H$_{24}$N$_2$O$_5$:
Calculated: 396.1688.
Found: 396.1694.

EXAMPLE 42

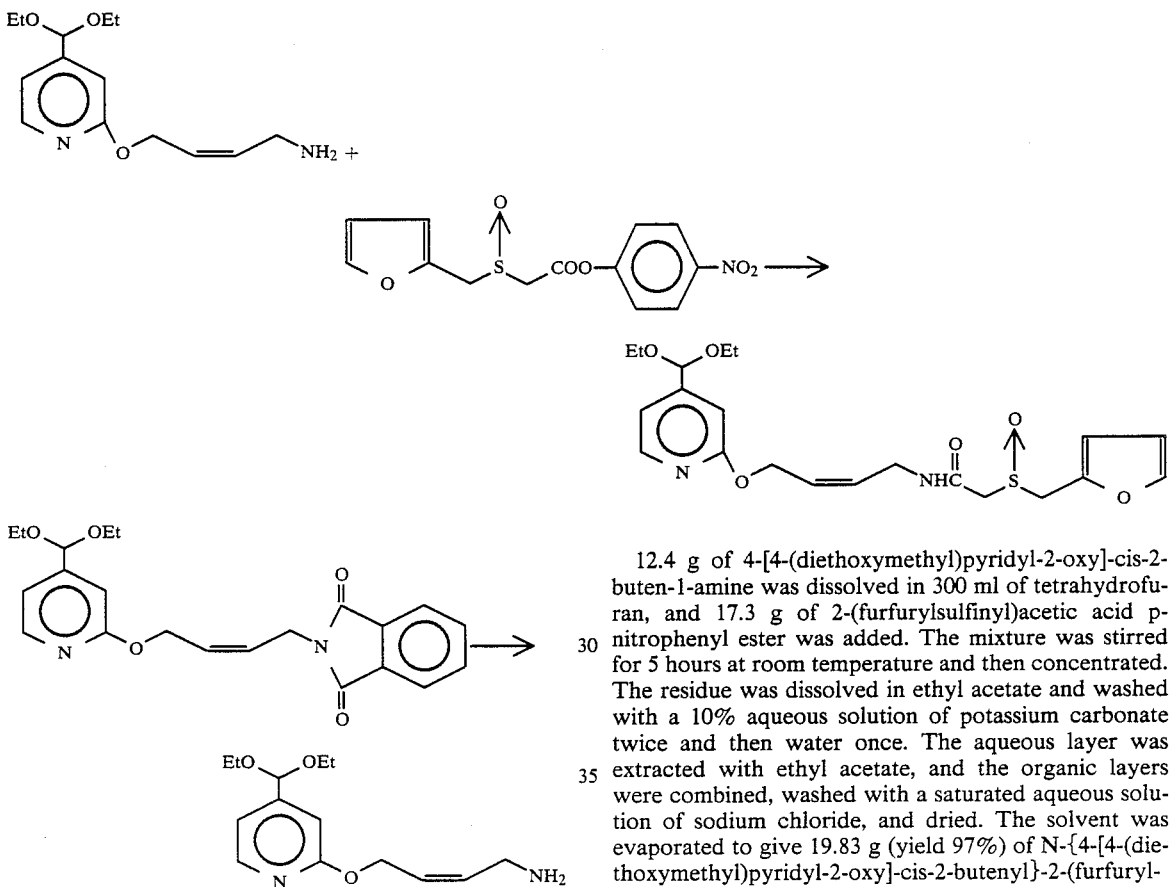

41.06 g of N-{4-[4-(diethoxymethyl)pyridyl-2-oxy]-cis-2-butene}phthalimide was dissolved in 500 ml of methanol, and 13.93 g of hydrazine monohydrate was added. The mixture was refluxed for 2 hours. The reaction mixture was concentrated, and the residue was diluted with methylene chloride. The insoluble matter was separated by filtration, and the solid was washed with methylene chloride. The filtrate and the washing were combined and concentrated. Methylene chloride was added to the concentrate, and the mixture was repeatedly filtered, and washed until no solid precipitated. The concentrate was dissolved in ethyl acetate and washed twice with water. The organic layer was extracted with cold 10% acetic acid. The extract (acetic acid solution) was made basic by adding solid anhydrous potassium carbonate under ice cooling, and the solution was extracted twice with ethyl acetate, washed with a saturated aqueous solution of sodium chloride, and dried. The solvent was evaporated to give 12.4 g (yield 50.2%) of 4-[4-(diethoxymethyl)pyridyl-2-oxy]-cis-2-buten-1-amine.

$^1$H -NMR ($\delta$, CDCl$_3$): 1.23 (6H, t, J=9 Hz), 1.55 (2H, brs), 3.45 (2H, d, J=4.8 Hz), 3.55 (4H, m), 4.89 (2H, d, J=5.4 Hz), 5.43 (1H, s), 5.75 (2H, m), 6.87 (1H, s), 6.97 (1H, d, J=4.5 Hz), 8.13 (1H, d, J=4.5 Hz).

IR (cm$^{-1}$ film): 3400, 3200, 3000, 2950, 1680, 1620, 1570, 1410, 1060.

Mass: as C$_{14}$H$_{22}$N$_2$O$_3$:
Found: 266.1642.
Calculated: 266.1641.

EXAMPLE 43

12.4 g of 4-[4-(diethoxymethyl)pyridyl-2-oxy]-cis-2-buten-1-amine was dissolved in 300 ml of tetrahydrofuran, and 17.3 g of 2-(furfurylsulfinyl)acetic acid p-nitrophenyl ester was added. The mixture was stirred for 5 hours at room temperature and then concentrated. The residue was dissolved in ethyl acetate and washed with a 10% aqueous solution of potassium carbonate twice and then water once. The aqueous layer was extracted with ethyl acetate, and the organic layers were combined, washed with a saturated aqueous solution of sodium chloride, and dried. The solvent was evaporated to give 19.83 g (yield 97%) of N-{4-[4-(diethoxymethyl)pyridyl-2-oxy]-cis-2-butenyl}-2-(furfurylsulfinyl)acetamide.

$^1$H -NMR ($\delta$, CDCl$_3$): 1.23 (6H, t, J=9 Hz), 3.33 (1H, d, J=14.4 Hz), 3.58 (5H, m), 4.11 (2H, t, J=6.6 Hz), 4.18 (1H, d, J=18.5 Hz), 4.27 (1H, d, J=18.5 Hz), 4.94 (2H, d, J=5.7 Hz), 5.43 (1H, s), 5.67 (1H, m), 5.86 (1H, m), 6.40 (1H, m), 6.47 (1H, d, J=3.3 Hz), 6.87 (1H, s), 6.98 (1H, d, J=5.4 Hz), 7.11 (1H, brs), 7.43 (1H, d, J=1.8 Hz), 8.12 (1H, d, J=5.1 Hz)

IR (cm$^{-1}$) 3400, 2950, 1680, 1620, 1570, 1400.

Mass: as C$_{21}$H$_{28}$N$_2$O$_6$S:
Found: 436.1676.
Calculated: 436.1668.

EXAMPLE 44

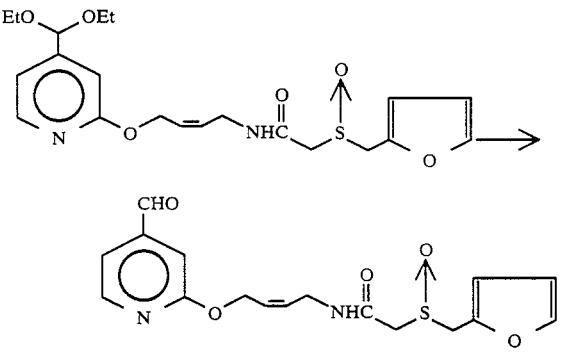

19.83 g of N-{4-[4-(diethoxymethyl)pyridyl-2-oxy]-cis-2-butenyl}-2-(furfurylsulfinyl)acetamide was dissolved in 600 ml of a 4:1 mixture of acetone-water, and 1.72 g of p- toluenesulfonic acid monohydrate was added. The mixture was refluxed for 3 hours. After cooling, the solution was concentrated. The residue was taken into ethyl acetate, and added to a cold saturated aqueous solution of sodium hydrogen carbonate. The precipitated insoluble matter was removed by filtration, and the organic layer was separated. The aqueous layer was extracted with ethyl acetate. The organic layers were combined, washed with a saturated aqueous solution of sodium chloride and dried. The solvent was evaporated to give 16.64 g of N-[4-(4-formyl-2-pyridyloxy)-cis-2-butenyl]-2-(furfurylsulfinyl)acetamide.

Yield: quantitative
Melting point: 67.6°–69.9 °C.

$^1$H -NMR (δ, CDCl$_3$): 10.00 (1H, s), 8.36 (1H, d, J=4.6 Hz), 7.45 (1H, d, J=3 Hz), 7.30 (1H, d, J=4.6 Hz), 7.16 (1H, s), 7.08 (1H, brs), 6.47 (1H, d, J=3.5 Hz), 6.40 (1H, dd, J=3.5, 3.0 Hz), 5.82–5.92 (1H, m), 5.66–5.76 (1H, m), 5.00 (2H, d, J=6.4 Hz), 4.27 (1H, d, J=14.3 Hz), 4.18 (1H, d, J=14.3 Hz), 4.12 (2H, t, J=6.3 Hz), 3.59 (1H, d, J=14.1 Hz), 3.34 (1H, d, J=14.1 Hz).

IR (cm$^{-1}$, KBr): 3236, 1712, 1624, 1564, 1036.

Mass: as C$_{17}$H$_{18}$N$_2$O$_5$S:
Found: 362.0934.
Calculated: 362.0937.

The following are specific formulation examples of medicaments using the compounds of the present invention.

Formulation Example A (tablet)

Recipe I-a (for preparation of tablets each containing 30 mg of the compound prepared in Example 2 as the active ingredient)

| | |
|---|---|
| N-{4-[4-(piperidinomethyl)pyridyl-2-oxy]-cis-2-butenyl}-2-(furfuryl-sulfinyl)acetamide | 30 (mg/tablet) |
| lactose | 60.3 |
| corn starch | 15.10 |
| carboxymethyl cellulose calcium | 12 |
| methyl cellulose (25 cps) | 2 |
| magnesium stearate | 0.6 |
| | 120 |

Recipe I-b (for preparation of tablets each containing 60 mg of the compound prepared in Example 2 as the active ingredient)

| | |
|---|---|
| N-{4-[4-(piperidinomethyl)pyridyl-2-oxy]-cis-2-butenyl}-2-(furfuryl-sulfinyl)acetamide | 60 (mg/tablet) |
| lactose | 90.6 |
| corn starch | 25.0 |
| carboxymethyl cellulose calcium | 20 |
| methyl cellulose (25 cps) | 3.4 |
| magnesium stearate | 1.0 |
| | 200 |

N-{4-[4-(piperidinomethyl)pyridyl-2-oxy]-cis-2-butenyl}-2-(furfurylsulfinyl)acetamide, lactose, corn starch and carboxymethyl cellulose calcium were mixed. A solution of methyl cellulose (25 cps) in deionized water was added. They were kneaded, then granulated, and sized. The granules were mixed further with magnesium stearate. The mixture was tableted to give tablets each containing 30 or 60 mg of the above active compound.

Formulation Example B (capsule)

Recipe II (for preparation of capsules each containing 30 mg of the compound obtained in Example 2 as the active ingredient per capsule)

| | |
|---|---|
| N-{4-[4-(piperidinomethyl)pyridyl-2-oxy]-cis-2-butenyl}-2-(furfuryl-sulfinyl)acetamide | 30 (mg/capsule) |
| lactose | 40. |
| corn starch | 38.8 |
| magnesium stearate | 1.2 |
| | 110 |

N-{4-[4-(piperidinomethyl)pyridyl-2-oxy]-cis-2-butenyl}-2-(furfurylsulfinyl)acetamide was thoroughly pulverized, and well mixed with lactose, corn starch and magnesium stearate. The mixture was filled into No. 5 capsules.

What is claimed is:

1. A compound represented by the following formula

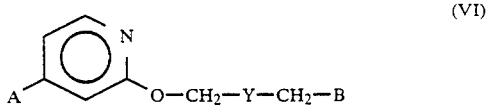

(VI)

wherein A represents a formyl group, a formyl group protected by a lower alcohol, a lower alkylene group or a lower alkylester of orthoformic acid, a hydroxymethyl group, or a hydroxymethyl group in which the hydroxyl group is protected by a protective group which can be split off by hydrolysis and which is selected from the group consisting of tetrahydropyranyl group, lower alkoxyalkyl group, aralkyl group and silyl group, B represents a halogen atom, an amino group, a phthalimide group, a hydroxyl group or a hydroxyl group protected by a protective group which can be split off by hydrolysis and which is selected from the group consisting of tetrahydropyranyl group, lower alkoxyalkyl group, aralkyl group and silyl group, and Y represents —CH$_2$—CH$_2$— or —CH=CH—.

2. A compound represented by the following formula

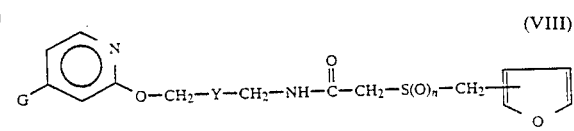

(VIII)

wherein G represents a formyl group, a formyl group protected by a lower alcohol, a lower alkylene group or a lower alkylester of orthoformic acid, a hydroxymethyl group, a hydroxymethyl group in which the hydroxyl group is protected by a protective group which can be split off by hydrolysis and which is selected from the group consisting of tetrahydropyranyl group, lower alkoxyalkyl group, aralkyl group and a silyl group, or a halogenomethyl group, Y represents —CH$_2$—CH$_2$— or —CH=CH—, and n is 0, 1 or 2.

3. The compound of claim 2 wherein G represents a formyl group.

4. The compound of claim 2 wherein G represents a formyl group protected by methanol, ethanol, propanol, 1,2-ethylene glycol, 1,3-propylene glycol, methylorthoformate or ethylorthoformate.

5. The compound of claim 2 wherein G represents a protected formyl group which is 2-(1,3-dioxolane), 2-(1,3-dioxane), dimethylacetal, diethylacetal, or dipropylacetal.

6. The compound of claim 2 wherein G represents a halogenomethyl group.

7. The compound of claim 2 wherein Y represents $-CH_2-CH_2-$.

8. The compound of claim 2 wherein Y represents $-CH=CH-$.

9. The compound of claim 2 wherein n is 0.

10. The compound of claim 2 wherein n is 1.

11. The compound of claim 2 wherein n is 2.

12. The compound of claim 1 wherein A represents a formyl group.

13. The compound of claim 1 wherein A represents a formyl group protected by methanol, ethanol, propanol, 1,2-ethylene glycol, 1,3-propylene glycol, methylorthoformate or ethylorthoformate.

14. The compound of claim 1 wherein A represents the protected formyl group which is 2-(1,3dioxolane), 2-(1,3-dioxane), dimethylacetal, diethylacetal, or dipropylacetal.

15. The compound of claim 1 wherein B represents a halogen atom.

16. The compound of claim 1 wherein B represents a phthalimide group.

17. The compound of claim 1 wherein B represents a hydroxyl group.

18. The compound of claim 1 wherein B represents said protected hydroxyl group.

19. The compound of claim 1 wherein Y represents $-CH_2-CH_2-$.

20. The compound of claim 1 wherein Y represents $-CH=CH-$.

* * * * *